United States Patent
Semenov

(10) Patent No.: US 9,724,010 B2
(45) Date of Patent: Aug. 8, 2017

(54) SYSTEMS AND METHODS OF 4D ELECTROMAGNETIC TOMOGRAPHIC (EMT) DIFFERENTIAL (DYNAMIC) FUSED IMAGING

(75) Inventor: Serguei Y. Semenov, Tittensor (GB)

(73) Assignee: EMTensor GmbH, Vienna (AT)

( * ) Notice: Subject to any disclaimer, the term of this patent is extended or adjusted under 35 U.S.C. 154(b) by 24 days.

(21) Appl. No.: 13/173,078

(22) Filed: Jun. 30, 2011

(65) Prior Publication Data

US 2012/0010493 A1    Jan. 12, 2012

Related U.S. Application Data

(60) Provisional application No. 61/362,634, filed on Jul. 8, 2010.

(51) Int. Cl.
G06K 9/00 (2006.01)
A61B 5/05 (2006.01)
A61B 5/00 (2006.01)

(52) U.S. Cl.
CPC .......... *A61B 5/0507* (2013.01); *A61B 5/0035* (2013.01); *A61B 5/05* (2013.01); *A61B 5/7257* (2013.01)

(58) Field of Classification Search
CPC ... A61B 5/7257; A61B 5/0507; A61B 5/0035; A61B 5/05
(Continued)

(56) References Cited

U.S. PATENT DOCUMENTS 4,135,131 A    1/1979 Larsen et al.
4,157,472 A    6/1979 Beck, Jr. et al.
(Continued)

FOREIGN PATENT DOCUMENTS

EP    2404550 A1    1/2012
EP    2404550 B1    11/2015
(Continued)

OTHER PUBLICATIONS

Serguei Semenov: "Microwave tomography: review of the progress towards clinical applications", Philosophical Transactions of the Royal Society, vol. 2009, No. 367, Dec. 31, 2009. [pp. 3021-3042, XP002661164. DOI: 10.1098/rsta.2009.0092.
(Continued)

*Primary Examiner* — Jennifer Dieterle
*Assistant Examiner* — Helene Bor
(74) *Attorney, Agent, or Firm* — Tillman Wright, PLLC; James D. Wright; David R. Higgins

(57) ABSTRACT

Methods and systems for 4D electromagnetic tomographic differential (dynamic) fused imaging and mapping of electrical excitation of biological tissues. A plurality of electromagnetic field sources and detectors generate and detect an electromagnetic field domain in a target area. A biological tissue is positioned within the target area, and an electromagnetic field domain is generated via a selected plurality of sources. The field generated by each source is selectively characterized so that each of a selected plurality of detectors recognizes a source of field from the plurality of sources. The sources and detectors are controlled so that fields generated by the selected sources are received by the selected detectors after interacting with the tissue. Based on the field received at each detector, a complex interference (scattering) matrix is derived from the tissue-generated field, and anatomical and functional image information are reconstructed from this matrix. The anatomical information and functional information are fused for display.

19 Claims, 20 Drawing Sheets
(7 of 20 Drawing Sheet(s) Filed in Color)

(58) Field of Classification Search
USPC .......................... 606/425; 600/407; 324/637
See application file for complete search history.

(56) References Cited

U.S. PATENT DOCUMENTS

| | | | |
|---|---|---|---|
| 4,247,815 | A | 1/1981 | Larsen et al. |
| 4,638,813 | A | 1/1987 | Turner |
| 4,662,222 | A | 5/1987 | Johnson |
| 4,798,209 | A | 1/1989 | Klingenbeck et al. |
| 4,805,627 | A | 2/1989 | Klingenbeck et al. |
| 4,926,868 | A | 5/1990 | Larsen |
| 5,069,223 | A | 12/1991 | McRae |
| 5,222,501 | A | 6/1993 | Ideker et al. |
| 5,233,713 | A | 8/1993 | Murphy et al. |
| 5,263,050 | A | 11/1993 | Sutterlin et al. |
| 5,305,748 | A | 4/1994 | Wilk |
| 5,363,050 | A | 11/1994 | Guo et al. |
| 5,405,346 | A | 4/1995 | Grundy et al. |
| 5,715,819 | A | 2/1998 | Svenson et al. |
| 6,026,173 | A * | 2/2000 | Svenson et al. .............. 382/131 |
| 6,073,047 | A | 6/2000 | Barsamian et al. |
| 6,332,087 | B1 | 12/2001 | Svenson et al. |
| 6,333,087 | B1 | 12/2001 | Jerdee et al. |
| 6,490,471 | B2 | 12/2002 | Svenson et al. |
| 6,503,203 | B1 * | 1/2003 | Rafter et al. .................. 600/458 |
| 6,522,910 | B1 | 2/2003 | Gregory |
| 6,697,660 | B1 * | 2/2004 | Robinson ...................... 600/409 |
| 6,865,494 | B2 | 3/2005 | Duensing et al. |
| 7,239,731 | B1 * | 7/2007 | Semenov et al. ............. 382/128 |
| 7,272,431 | B2 * | 9/2007 | McGrath ....................... 600/509 |
| 7,340,292 | B2 | 3/2008 | Li |
| 7,876,114 | B2 | 1/2011 | Campbell et al. |
| 8,000,775 | B2 | 8/2011 | Pogue et al. |
| 8,089,417 | B2 | 1/2012 | Popovic et al. |
| 8,207,733 | B2 | 6/2012 | Meaney et al. |
| 8,253,619 | B2 | 8/2012 | Holbrook et al. |
| 8,376,948 | B2 | 2/2013 | Brannan |
| 8,724,864 | B2 | 5/2014 | Persson et al. |
| 9,072,449 | B2 | 7/2015 | Semenov |
| 9,414,749 | B2 | 8/2016 | Semenov |
| 9,414,763 | B2 | 8/2016 | Semenov |
| 9,414,764 | B2 | 8/2016 | Semenov |
| 2002/0168317 | A1 | 11/2002 | Daighighian et al. |
| 2002/0191744 | A1 | 12/2002 | Mirabelle |
| 2003/0018244 | A1 | 1/2003 | Haddad et al. |
| 2003/0088180 | A1 | 5/2003 | Van Veen et al. |
| 2003/0090276 | A1 | 5/2003 | Weide et al. |
| 2004/0123667 | A1 | 7/2004 | McGrath |
| 2004/0174948 | A1 | 9/2004 | Kojima et al. |
| 2006/0133564 | A1 * | 6/2006 | Langan et al. .................... 378/8 |
| 2006/0247531 | A1 | 11/2006 | Pogue et al. |
| 2007/0025514 | A1 | 2/2007 | Lawaczeck |
| 2007/0238957 | A1 * | 10/2007 | Yared ............................ 600/407 |
| 2008/0319437 | A1 | 12/2008 | Turner et al. |
| 2009/0015832 | A1 | 1/2009 | Popovic et al. |
| 2010/0010340 | A1 | 1/2010 | Godavarty et al. |
| 2010/0067770 | A1 | 3/2010 | Persson et al. |
| 2010/0174179 | A1 | 7/2010 | Persson et al. |
| 2011/0022325 | A1 | 1/2011 | Craddock et al. |
| 2011/0263961 | A1 | 10/2011 | Craddock et al. |
| 2011/0295102 | A1 | 12/2011 | Lakkis et al. |
| 2012/0083683 | A1 | 4/2012 | Kuwabara |
| 2012/0083690 | A1 | 4/2012 | Semenov |
| 2012/0172954 | A1 | 7/2012 | Zastrow et al. |
| 2012/0179037 | A1 | 7/2012 | Halmann |
| 2012/0190977 | A1 | 7/2012 | Persson et al. |
| 2014/0024917 | A1 | 1/2014 | McMahon et al. |
| 2014/0155740 | A1 | 6/2014 | Semenov |
| 2014/0275944 | A1 | 9/2014 | Semenov |
| 2014/0276012 | A1 | 9/2014 | Semenov |
| 2014/0378812 | A1 | 12/2014 | Saroka et al. |
| 2015/0257648 | A1 | 9/2015 | Semenov |
| 2015/0257649 | A1 | 9/2015 | Semenov |
| 2015/0342472 | A1 | 12/2015 | Semenov |
| 2016/0256109 | A1 | 9/2016 | Semenov |
| 2016/0262623 | A1 | 9/2016 | Semenov |
| 2016/0345856 | A1 | 12/2016 | Semenov |

FOREIGN PATENT DOCUMENTS

| | | |
|---|---|---|
| EP | 3037035 A1 | 6/2016 |
| IL | 241603 | 10/2016 |
| RU | 2449729 C2 | 5/2012 |
| RU | 2596984 C2 | 9/2016 |
| RU | 2603613 C1 | 11/2016 |
| WO | 9532665 | 12/1995 |
| WO | 9852464 A1 | 11/1998 |
| WO | 0015109 A1 | 3/2000 |
| WO | 2005115235 A1 | 12/2005 |
| WO | 2007136334 A1 | 11/2007 |
| WO | 2008002251 A1 | 1/2008 |
| WO | 2010100649 A1 | 9/2010 |
| WO | 2011009945 A2 | 1/2011 |
| WO | 2011156810 A2 | 12/2011 |
| WO | 2011156810 A3 | 12/2011 |
| WO | 2013005134 A2 | 1/2013 |
| WO | 2013005134 A3 | 1/2013 |
| WO | 2014081992 A2 | 5/2014 |
| WO | 2014150616 A2 | 9/2014 |
| WO | 2014150618 A1 | 9/2014 |
| WO | 2014150616 A3 | 12/2014 |
| WO | 2014081992 A3 | 8/2015 |

OTHER PUBLICATIONS

Semenov S Y et al: "Development of microwave tomography for functional cardiac imaging", Biomedical Imaging: Macro to Nano, 2004, Piscataway, NJ, USA, IEEE, Apr. 15, 2004, pp. 1351-1353, XP010774114, DOI: 10.1109/ISBI.2004.1398797 ISBN: 978-0-7803-8389-0.
"European Search Report" and "Written Opinion of the European Patent Office" in European Patent Application No. 11275103.7 for EMImaging Limited, dated Oct. 13, 2011, 5 pages.
"International Search Report" and "Written Opinion of the International Searching Authority" (ISA/US) in Emtensor GMBH, International Patent Application Serial No. PCT/US2014/023803, mailed Jun. 25, 2014 (9 pages).
Information Disclosure Statement (IDS) Letter Regarding Common Patent Application(s), dated Jan. 26, 2015.
Fear, Elise C., et al. "Confocal microwave imaging for breast cancer detection: Localization of tumors in three dimensions." IEEE Transactions of Biomedical Engineering 49.8 (2002): 812-822 (11 pages).
Yaniv, Ziv, et al. "Electromagnetic tracking in the clinical environment." Medical physics 36.3 (2009): 876-892 (17 pages).
"International Search Report" and "Written Opinion of the International Searching Authority" (ISA/US) in Emtensor GMBH, International Patent Application Serial No. PCT/US2014/023793, mailed Oct. 31, 2014 (11 pages).
"International Search Report" and "Written Opinion of the International Searching Authority" (ISA/US) in Emtensor GMBH, International Patent Application Serial No. PCT/US2013/071360, mailed May 27, 2014 (20 pages).
Information Disclosure Statement (IDS) Letter Regarding Common Patent Application(s), dated Jun. 27, 2015.
Information Disclosure Statement (IDS) Letter Regarding Common Patent Application(s), dated May 10, 2016.
Information Disclosure Statement (IDS) Letter Regarding Common Patent Application(s), dated Feb. 3, 2017.
"International Preliminary Report on Patentability" of the International Bureau of WIPO in Emtensor GMBH, International Patent Application Serial No. PCT/US2013/071360, sent Jul. 7, 2015 (17 pages).
"Extended European Search Report," European Patent Application No. 14768384.1, for EMTensor GmbH, et al., dated Oct. 20, 2016 (7 pages).
"Extended European Search Report," European Patent Application No. 13856581.7, for EMTensor GmbH, et al., dated Aug. 25, 2016 (7 pages).

(56) References Cited

OTHER PUBLICATIONS

"Extended European Search Report," European Patent Application No. 15193895.8, for EMTensor GmbH, dated May 25, 2016 (6 pages).
"Extended European Search Report," European Patent Application No. 14768372.6, for EMTensor GmbH, et al., dated Sep. 16, 2016 (10 pages).
Jofre, L., et al., "Medical Imaging with a Microwave Tomographic Scanner," IEEE Transactions on Biomedical Engineering (Mar. 1990), pp. 303-312, vol. 37, No. 3 (10 pages).
Semenov, S.Y., et al., "Dielectrical Model of Cellular Structures in Radio Frequency and Microwave Spectrum, Electrically Interacting Versus Noninteracting Cells," Annals of Biomedical Engineering (2001), pp. 427-435, vol. 29, No. 5, published by Biomedical Engineering Society (9 pages).
Hawley, M.S., et al., "Microwave Imaging of Tissue Blood Content Changes," Journal of Biomedical Engineering (1991), pp. 197-202, vol. 13, No. 3, published by Butterworth-Heinermann for BES (6 pages).
Semenov, S., et al., "Microwave Tomography of Extremities: 1. Dedicated 2D System and Physiological Signatures," Physics in Medicine and Biology (2011), pp. 2005-2017, vol. 56, No. 7, published by Institute of Physics and Engineering in Medicine, United Kingdom (13 pages).
Semenov, S.Y., et al., "Myocardial Ischemia and Infarction Can Be Detected by Microwave Spectroscopy, 2. Biophysical Reconstruction," International Conference of the IEEE Engineering in Medicine and Biology Society (1996), pp. 1363-1364, vol. 4, published by IEEE (2 pages).

\* cited by examiner

SYSTEMS AND METHODS OF 4D ELECTROMAGNETIC TOMOGRAPHIC (EMT) DIFFERENTIAL (DYNAMIC) FUSED IMAGING

CROSS-REFERENCE TO RELATED APPLICATIONS

For purposes of the United States, the present application is a U.S. nonprovisional patent application of, and claims priority under 35 U.S.C. §119(e) to, U.S. provisional patent application Ser. No. 61/362,634, filed Jul. 8, 2010 and entitled "SYSTEMS AND METHODS OF 4D ELECTROMAGNETIC TOMOGRAPHIC (EMT) DIFFERENTIAL (DYNAMIC) FUSED IMAGING," which is expressly incorporated by reference herein. Additionally, the entirety of U.S. Pat. No. 7,239,731 to Semenov et al., issued Jul. 3, 2007 and entitled "SYSTEM AND METHOD FOR NON-DESTRUCTIVE FUNCTIONAL IMAGING AND MAPPING OF ELECTRICAL EXCITATION OF BIOLOGICAL TISSUES USING ELECTROMAGNETIC FIELD TOMOGRAPHY AND SPECTROSCOPY," is expressly incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to electromagnetic tomography, and, in particular but not exclusively, to 4D electromagnetic tomography for producing fused anatomical-functional images of biological objects.

Background

Electromagnetic tomography (EMT) is a relatively recent imaging modality with great potential for biomedical applications, including a non-invasive assessment of functional and pathological conditions of biological tissues. Using EMT, biological tissues are differentiated and, consequentially, can be imaged based on the differences in tissue dielectric properties. The dependence of tissue dielectric properties from its various functional and pathological conditions, such as blood and oxygen contents, ischemia and infarction malignancies has been demonstrated.

Two-dimensional (2D) and three-dimensional (3D) EMT systems and methods of image reconstruction have been developed over the last decade or more. Feasibility of the technology for various biomedical applications has been demonstrated, for example, for cardiac imaging and extremities imaging.

Complexity of EM Distribution within an Imaging Chamber: the Need to Diminish Effect from Boundaries.

As in any biomedical imaging, the classical EMT imaging scenario consists of cycles of measurements of complex signals, as scattered by a biologic object under study, obtained from a plurality of transmitters located at various points around the object and measured on a plurality of receivers located at various points around the object. This is illustrated in FIG. 1. As recounted elsewhere herein, the measured matrix of scattered EM signals may then be used in image reconstruction methods in order to reconstruct 3D distribution of dielectric properties of the object, i.e., to construct a 3D image of the object.

Generally, it is very important for image reconstruction to precisely describe a distribution of EM field with an imaging domain. The distribution of EM field with an imaging chamber is a very complex phenomenon, even when there is no object of interest inside.

There are also boundary problems arising from restricted volume of an imaging domain which needs to be taken into account or efforts made in order to diminish boundaries effect.

There are different ways for diminishing boundary effects. For example, boundary effects may be diminished by using an absorptive material(s), as described in U.S. Pat. No. 7,239,731, or boundary effects may be diminished by increasing the absorptive properties of a matching solution, conserving a sufficient level of the signal on receivers as described herein (see block "Attenuation vs boundary problem assessment block" in FIG. 11).

Recent Trends in Biomedical Imaging: Fused Images of Multi-modalities System.

Medical imaging plays a significant role in advances in modern non-invasive diagnostics, treatment planning and post-treatment follow-up studies. Recently medical imaging has expanded into dual- and multi-modality fusion of morphological/anatomical (for example, CT and MRI) and functional (for example, FDG-PET and DCE-MRI) imaging modalities. This significantly improves the diagnostic power while simultaneously increasing the cost of already expensive medical imaging devices and investigations.

An initial approach of software based image fusion suffered from significant problems caused by different patient position, motion, involuntary movement of internal organs. This lead to a fusion of different imaging modalities into a single imaging setting, rather than fusion of the images within a post-imaging procedure. One of the first dual-imaging system/combined PET/CT was developed at the University of Pittsburg Medical School. The combined PET/CT scanner was designed primarily for applications in clinical oncology. The first combined commercial PET/CT system approved by the FDA was manufactured by CTI PET Systems in 2000, shortly followed by GE Medical systems and Philips. It is now agreed that PET/CT is significantly more accurate than PET alone for the detection and localization of tumors and PET/CT is superior to PET alone in terms of sensitivity, specificity and accuracy, mainly because of the detection of new lesions. In addition, combined PET/CT allows for considerable gain of examination time within a single session.

Following the introduction of the PET/CT combination, various other combinations of different imaging modalities have been reported. Combined SPECT/CT has proven useful for cardiac, oncologic and neurologic applications. Combined 3D echocardiography and myocardial perfusion SPECT has been used for cardiac stress testing. MRI/CT image fusion is used in computer assisted surgery. The feasibility of fused whole-body MRI/FDG-PET for the evaluation of patients with cancer has been demonstrated. Authors of one study stated that "because some malignant tumors do not show increased glucose metabolism, the additional information provided by MRI brings substantial benefits."

Further on, dual-modality fused imaging has expanded into multi-modality imaging. Multi-modality fusion of morphological (CT and MRI) and functional (FDG-PET and DCE-MRI) images has been shown combining the three most clinically used tomographic imaging modalities (CT, MRI and PET) in treatment planning, navigation and follow up for radiofrequency ablation of tumors.

There is a recent trend in the development of medical imaging devices specifically dedicated for imaging of a certain diseases, for example cancer. This is significantly different from the concept of previous all-purpose system. For example, one study reported the construction of PET/CT scanner dedicated specifically for breast imaging. In this study, an FDG tracer was used and the duration of an imaging session was 12.5 min per breast.

As set forth above, multi-modality imaging significantly improves diagnostic power. However, it simultaneously increases the cost of already-costly medical devices. Further, multi-modalities imaging systems are very bulky and are not applicable for mobile settings. Thus, a need exists for systems, methods and approaches that provide fast, cost-efficient fused anatomical-functional imaging applicable, preferably for mobile settings.

SUMMARY OF THE PRESENT INVENTION

According to one or more aspects, the present invention comprises a novel imaging concept of four-dimensional (4D) electromagnetic (EMT) imaging: 3D in the spatial domain plus the additional "one-dimension" (1D) in time, functional dynamic domain. In 4D EMT imaging, instead of a fusion of images obtained by different imaging modalities, 4D EMT imaging fuses absolute anatomical images with dynamic, differential images acquired by the same imaging technology. A novel concept allows for functional fused imaging of tissues using rapid EMT alone, with potentials for mobile and low cost settings. An additional advantage of the concept is the mobility of EMT. It is expected that systems will be applicable for "bed-side functional imaging" or could be placed in an emergency land or aerial vehicle such as an ambulance or helicopter.

Broadly defined, the present invention according to one aspect is a method for functional imaging of, and non-invasive assessment of a spread of electrical excitation within, biological tissues, including: providing a plurality of electromagnetic field sources for generating an electromagnetic field domain in a target area; providing a plurality of electromagnetic field detectors for detecting at least a portion of the electromagnetic field domain in the target area; positioning a biological tissue within the target area; generating an electromagnetic field domain via a selected plurality of the electromagnetic field sources; selectively characterizing the electromagnetic field generated by each electromagnetic field source so that each of a selected plurality of electromagnetic field detectors recognizes a source of electromagnetic field from a plurality of electromagnetic field sources; controlling the electromagnetic field sources and the electromagnetic field detectors, so that electromagnetic fields generated by the selected plurality of electromagnetic field sources are received by the selected plurality of the electromagnetic field detectors after interacting with the biological tissue; based at least in part upon the electromagnetic field received at each electromagnetic field detector, measuring interference characteristics of at least an electromagnetic field generated by the biological tissue; determining anatomical image information and functional image information, each pertaining to the biological tissue, from the measured interference characteristics; and fusing the anatomical image information and functional image information for display by imaging means.

In a feature of this aspect, determining functional image information includes dynamically deriving time-varying functional image information; and wherein fusing the anatomical image information and functional image information includes dynamically fusing the anatomical image information and time-varying functional image information. In a further feature, the method further includes introducing, into the biological tissue, a sensitive material characterized by having a dielectric property that is a function of the local electrical field generated within the biological tissue; and based upon the electromagnetic field received at each electromagnetic field detector, measuring interference characteristics of an electromagnetic field caused by an electric/dielectric object. In a still further feature, the method further includes synchronizing the generating step with an electrical signal representative of an electrical excitation within the biological tissue. In a yet still further feature, the measured interference characteristics comprise a complex matrix.

In a further feature, the biological tissue in the positioning, controlling, determining, introducing, and both measuring steps includes cardiac tissue, and wherein the electrical signal in the synchronizing step is an electrocardiogram. In further variations of this feature, the biological tissue in the positioning, controlling, determining, introducing, and both measuring steps includes nervous tissue, and wherein the electrical signal in the synchronizing step is an electrical signal representative of an electrical excitation of the nervous tissue; the biological tissue in the positioning, controlling, determining, introducing and both measuring steps includes musculoskeletal tissue, and wherein the electrical signal in the synchronizing step is an electrical signal representative of an electrical excitation of the musculoskeletal tissue; and/or the biological tissue in the positioning, controlling, determining, introducing, and both measuring steps includes biological tissue, wherein the method further includes displaying, by functional imaging means, areas of particular functional and pathological conditions of the biological tissue, and wherein the particular functional and pathological conditions of the biological tissue include at least one of tissue blood content, ischemia, infraction, hypoxia, malignancies, benign tumor, edema, and temperature.

In another further feature, the providing steps include providing a plurality of integrated electromagnetic field source-detectors for generating an electromagnetic field domain in a target area and detecting at least a portion of the electromagnetic field domain in the target area.

In another further feature, the sensitive material in the introducing step is a multiple component media or nanoparticles that includes ferroelectric grains of different sizes. In further variations of this feature, at least some of the ferroelectric grains in the introducing step are formed from barium modified strontium titanium oxide; and/or the ferroelectric grains in the introducing step have different shapes, including spheres, ellipsoids and cylinders.

In another further feature, the sensitive material in the introducing step is a multiple component media that includes potentiometric liquid crystals. In a further variation of this feature, the potentiometric liquid crystals in the introducing step include MBBA, 7CB.

In another further feature, the sensitive material in the introducing step is a multiple component media includes a potentiometric dye. In a further variation of this feature, the potentiometric dye in the introducing step includes at least one of merocyanine, rhodamine, cyanine, oxonol or naphthyl styryl.

In another further feature, the introducing step includes injecting the sensitive material into the biological tissue.

In another further feature, the method also includes, as a preliminary step, disposing a system for carrying out the recited steps in a mobile land or aerial vehicle.

In another further feature, the method also includes identifying, based on the image information, an area of diseased tissue, and mapping electrical potentials in the area of diseased tissue to identify a source of functional irregularity or assess tissue functional viability.

Broadly defined, the present invention according to another aspect is a system for functional imaging of, and non-invasive assessment of a spread of electrical excitation within, biological tissues, including: a plurality of electromagnetic field source for generating an electromagnetic field domain in a target area; a plurality of electromagnetic field detectors for detecting at least a portion of the electromagnetic field domain in the target area; a working chamber for positioning a biological tissue within the target area; a controller, operably coupled to the plurality of electromagnetic field sources and the electromagnetic field detectors to cause electromagnetic fields generated by a selected plurality of the electromagnetic field sources to be received by a selected plurality of the electromagnetic field detectors after interacting with the biological tissue; a module for measuring interference characteristics of the electromagnetic field caused at least by the electromagnetic field generated by the biological tissue; an imaging computer for determining a fused anatomical and functional image of the biological tissue and the spread of electrical excitation in the biological tissue by inversing the electromagnetic fields detected by the plurality of electromagnetic field detectors; and a graphical display for displaying the fused anatomical and functional image of the biological tissue.

In a feature of this aspect, the imaging computer includes operational blocks that dynamically derive time-varying functional image information and dynamically fuse the anatomical image information and time-varying functional image information. In a further feature, the plurality of electromagnetic field sources, plurality of electromagnetic field detectors and working chamber are disposed in a mobile vehicle. In a still further feature, the system further includes a sensitive material, introduced into the biological tissue, that is characterized by having a dielectric property that is a function of the local electrical field that is generated within the biological tissue; and a module for measuring interference characteristics of the electromagnetic field caused by an electric/dielectric object. In a yet still further feature, the system further includes a reference module for synchronizing the generation of electromagnetic fields with an electrical signal representative of an electrical excitation of the biological tissue.

In a further feature, the biological tissue includes cardiac tissue, and wherein the generation of electromagnetic fields is synchronized with an electrocardiogram.

In another further feature, the biological tissue includes nervous tissue, and wherein the generation of electromagnetic fields is synchronized with an electrical signal representative of an electrical excitation of the nervous tissue.

In another further feature, the biological tissue includes musculoskeletal tissue, and wherein the generation of electromagnetic fields is synchronized with an electrical signal representative of an electrical excitation of musculoskeletal tissue.

In another further feature, the graphical display includes at least one image, of a particular functional or pathological condition of the biological tissue, on which the fused anatomical and functional image of the biological tissue is overlaid. In a further variation of this feature, the at least one image or a particular functional or pathological condition of the biological tissue includes an image of at least one of tissue blood content, ischemia, infraction, hypoxia, malignancies, benign tumor, edema, and temperature.

In another further feature, each electromagnetic field source is integrated with an electromagnetic field detector in a single module.

In another further feature, the sensitive material is a multiple component media or nanoparticles that includes ferroelectric grains of different sizes. In further variations of this feature, at least some of the ferroelectric grains are formed from barium modified strontium titanium oxide; and/or the ferroelectric grains have different shapes, including spheres, ellipsoids and cylinders.

In another further feature, the sensitive material is a multiple component media that includes potentiometric liquid crystals. In a further variation of this feature, the potentiometric liquid crystals include MBBA, 7CB.

In another further feature, the sensitive material is a multiple component media includes a potentiometric dye. In a further variation of this feature, the potentiometric dye includes at least one of merocyanine, rhodamine, cyanine, oxonol or naphthyl styryl.

In another feature of this aspect, the system is disposed in a mobile land or aerial vehicle.

Broadly defined, the present invention according to another aspect is a method of 4D electromagnetic tomographic (EMT) dynamic fused imaging of biological tissues, including: providing a plurality of electromagnetic field sources for generating an electromagnetic field domain in a target area; providing a plurality of electromagnetic field detectors for detecting at least a portion of the electromagnetic field domain in the target area; positioning a biological tissue within the target area; generating an electromagnetic field domain via a selected plurality of the electromagnetic field sources; selectively characterizing the electromagnetic field generated by each electromagnetic field source so that each of a selected plurality of electromagnetic field detectors recognizes a source of electromagnetic field from a plurality of electromagnetic field sources; controlling the electromagnetic field sources and the electromagnetic field detectors, so that electromagnetic fields generated by the selected plurality of electromagnetic field sources are received by the selected plurality of the electromagnetic field detectors after interacting with the biological tissue; based at least in part upon the electromagnetic field received at each electromagnetic field detector, measuring interference characteristics of at least an electromagnetic field generated by the biological object; providing an imaging computer having an attenuation versus boundary problems assessment block, an images reconstruction block, a differential image formation block, a motion correction block, and fused images formation block; and using the imaging computer, producing 4D fused anatomical and functional images for display by graphical means.

In a feature of this aspect, using the imaging computer includes dynamically deriving time-varying functional image information, and producing fused anatomical and functional images includes dynamically fusing anatomical image information and the time-varying functional image information. In a further feature, the method further includes: introducing, into the biological object, a sensitive material characterized by having a dielectric property that is a function of the local electrical field generated within the biological tissue; and based upon the electromagnetic field received at each electromagnetic field detector, measuring interference characteristics of an electromagnetic field caused by an electric/dielectric object. In a still further feature, the method further includes synchronizing the generating step with an electrical signal representative of an electrical excitation of the biological object. In a yet still further feature, the measured interference characteristics comprise a complex matrix.

In a further feature, the biological object in the positioning, controlling, producing, introducing, and both measuring steps includes cardiac tissue, and wherein the electrical signal in the synchronizing step is an electrocardiogram.

In another further feature, the biological object in the positioning, controlling, producing, introducing, and both measuring steps includes nervous tissue, and wherein the electrical signal in the synchronizing step is an electrical signal representative of an electrical excitation of the nervous tissue.

In another further feature, the biological object in the positioning, controlling, producing, introducing and both measuring steps includes musculoskeletal tissue, and wherein the electrical signal in the synchronizing step is an electrical signal representative of an electrical excitation of the musculoskeletal tissue.

In another further feature, the method further includes displaying, by functional imaging means, areas of particular functional and pathological conditions of the biological tissue, wherein the particular functional and pathological conditions of the biological tissue include at least one of tissue blood content, ischemia, infraction, hypoxia, malignancies, benign tumor, edema, and temperature.

In another further feature, the steps of providing a plurality of electromagnetic field sources and providing a plurality of electromagnetic field detectors include providing a plurality of integrated electromagnetic field source-detectors for generating an electromagnetic field domain in a target area and detecting at least a portion of the electromagnetic field domain in the target area.

In another further feature, the sensitive material in the introducing step is a multiple component media or nanoparticles that includes ferroelectric grains of different sizes. In variations of this feature, at least some of the ferroelectric grains in the introducing step are formed from barium modified strontium titanium oxide; and/or the ferroelectric grains in the introducing step have different shapes, including spheres, ellipsoids and cylinders.

In another further feature, the sensitive material in the introducing step is a multiple component media that includes potentiometric liquid crystals. In a variation of this feature, the potentiometric liquid crystals in the introducing step include MBBA, 7CB.

In another further feature, the sensitive material in the introducing step is a multiple component media includes a potentiometric dye. In a variation of this feature, the potentiometric dye in the introducing step includes at least one of merocyanine, rhodamine, cyanine, oxonol or naphthyl styryl.

In another further feature, the biological object includes biological tissue, and wherein the introducing step includes injecting the sensitive material into the biological tissue.

In another further feature, the method also includes, as a preliminary step, disposing a system for carrying out the recited steps in a mobile land or aerial vehicle.

In another further feature, the method also includes identifying, based on the image information, an area of diseased tissue, and mapping electrical potentials in the area of diseased tissue to identify a source of functional irregularity or assess tissue functional viability.

Broadly defined, the present invention according to another aspect is a system for 4D electromagnetic tomographic (EMT) dynamic fused imaging of biological objects, including: a plurality of electromagnetic field sources for generating an electromagnetic field domain in a target area; a plurality of electromagnetic field detectors for detecting at least a portion of the electromagnetic field domain in the target area; a working chamber for positioning a biological tissue within the target area; a controller, operably coupled to the plurality of electromagnetic field sources and the electromagnetic field detectors to cause electromagnetic fields generated by a selected plurality of the electromagnetic field sources to be received by a selected plurality of the electromagnetic field detectors after interacting with the biological tissue; a module for measuring interference characteristics of the electromagnetic field caused at least by the electromagnetic field generated by the biological tissue; and an imaging computer for determining a fused anatomical and functional image of the biological tissue, including an attenuation versus boundary problems assessment block, an images reconstruction block, a differential image formation block, a motion correction block, and fused images formation block.

In a feature of this aspect, the system further includes a graphical display for displaying the fused anatomical and functional image of the biological tissue.

In another feature of this aspect, the imaging computer further includes an EMT system setup and test block.

In another further feature of this aspect, the imaging computer further includes a know-how block.

In another further feature of this aspect, the operational blocks of the imaging computer dynamically derive time-varying functional image information and dynamically fuse the anatomical image information and time-varying functional image information to determine the fused anatomical and functional image of the biological tissue. In a further feature, the plurality of electromagnetic field sources, plurality of electromagnetic field detectors and working chamber are disposed in a mobile vehicle. In a still further feature, the system further includes: a sensitive material, introduced into the biological tissue, that is characterized by having a dielectric property that is a function of the local electrical field that is generated within the biological tissue; and a module for measuring interference characteristics of the electromagnetic field caused by an electric/dielectric object. In a yet still further feature, the system further includes a reference module for synchronizing the generation of electromagnetic fields with an electrical signal representative of an electrical excitation of the biological tissue.

In further features, the biological tissue includes cardiac tissue, wherein the generation of electromagnetic fields is synchronized with an electrocardiogram; the biological tissue includes nervous tissue, and the generation of electromagnetic fields is synchronized with an electrical signal representative of an electrical excitation of the nervous tissue; the biological tissue includes musculoskeletal tissue, and/or the generation of electromagnetic fields is synchronized with an electrical signal representative of an electrical excitation of musculoskeletal tissue.

In a still further feature, the graphical display includes at least one image, of a particular functional or pathological condition of the biological tissue, on which the fused anatomical and functional image of the biological tissue is overlaid. In a variation of this latter feature, the at least one image or a particular functional or pathological condition of the biological tissue includes an image of at least one of tissue blood content, ischemia, infraction, hypoxia, malignancies, benign tumor, edema, and temperature.

In a still further feature, each electromagnetic field source is integrated with an electromagnetic field detector in a single module.

In a still further feature, the sensitive material is a multiple component media or nanoparticles that includes ferroelectric grains of different sizes. In variations of this feature, at least some of the ferroelectric grains are formed from barium modified strontium titanium oxide; and/or the ferroelectric grains have different shapes, including spheres, ellipsoids and cylinders.

In a still further feature, the sensitive material is a multiple component media that includes potentiometric liquid crystals. In a variation of this feature, the potentiometric liquid crystals include MBBA, 7CB.

In a still further feature, the sensitive material is a multiple component media includes a potentiometric dye. In a variation of this feature, the potentiometric dye includes at least one of merocyanine, rhodamine, cyanine, oxonol or naphthyl styryl.

In another feature of this aspect, the system is disposed in a mobile land or aerial vehicle.

Broadly defined, the present invention according to another aspect is an imaging computer for determining a fused anatomical and functional image of the biological tissue in an EMT system, including: a know-how block; an attenuation versus boundary problems assessment block; an EMT system setup and test block; an images reconstruction block; a differential image formation block; a motion correction block; fused images formation block; and a graphical display for displaying the fused anatomical and functional image of the biological tissue.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features, embodiments, and advantages of the present invention will become apparent from the following detailed description with reference to the drawings, wherein.

DETAILED DESCRIPTION

Figure 1:
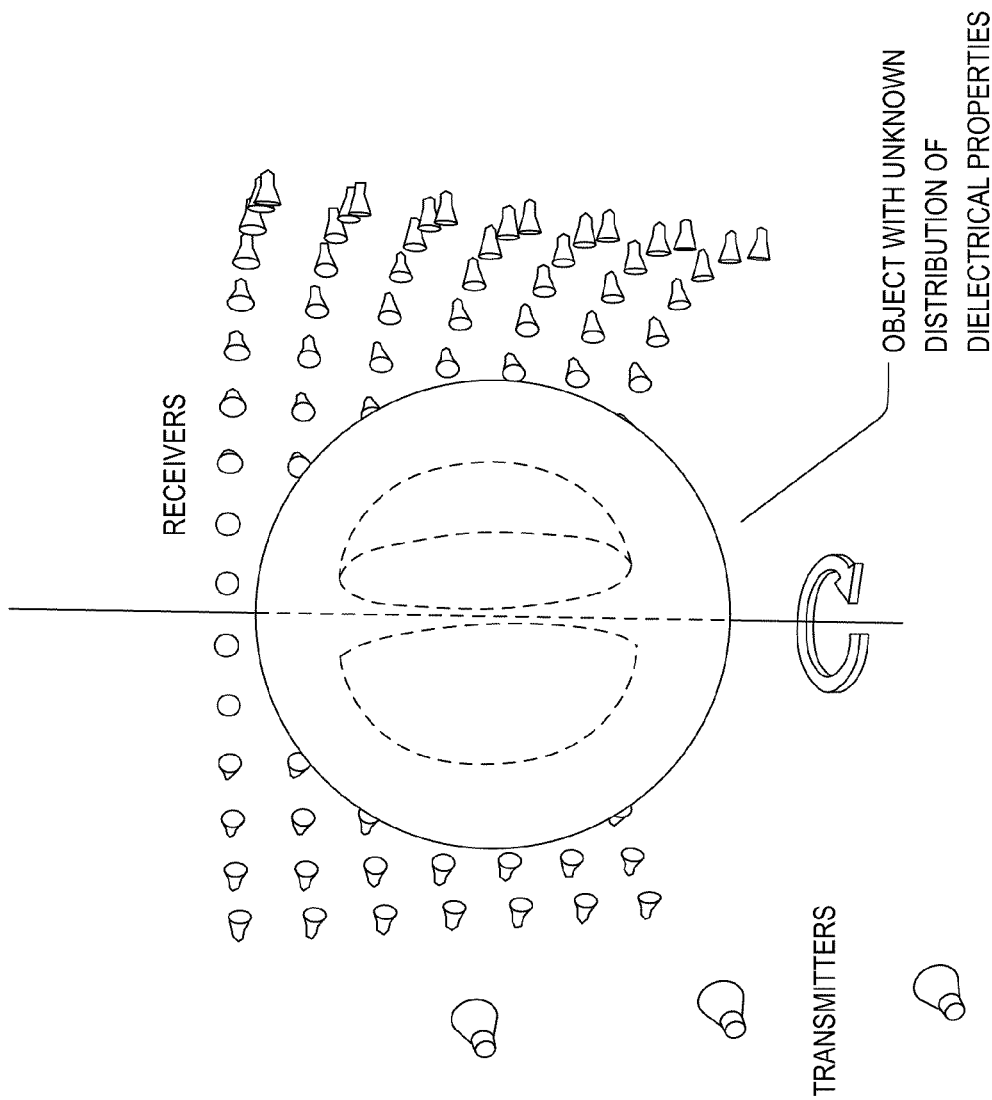
FIG. 1 is a graphical illustration of the principle of electromagnetic tomography (EMT)

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, the preferred embodiments of the present invention are next described. The following description of one or more preferred embodiment(s) is merely exemplary in nature and is in no way intended to limit the invention, its application, or uses.

Figure 2:
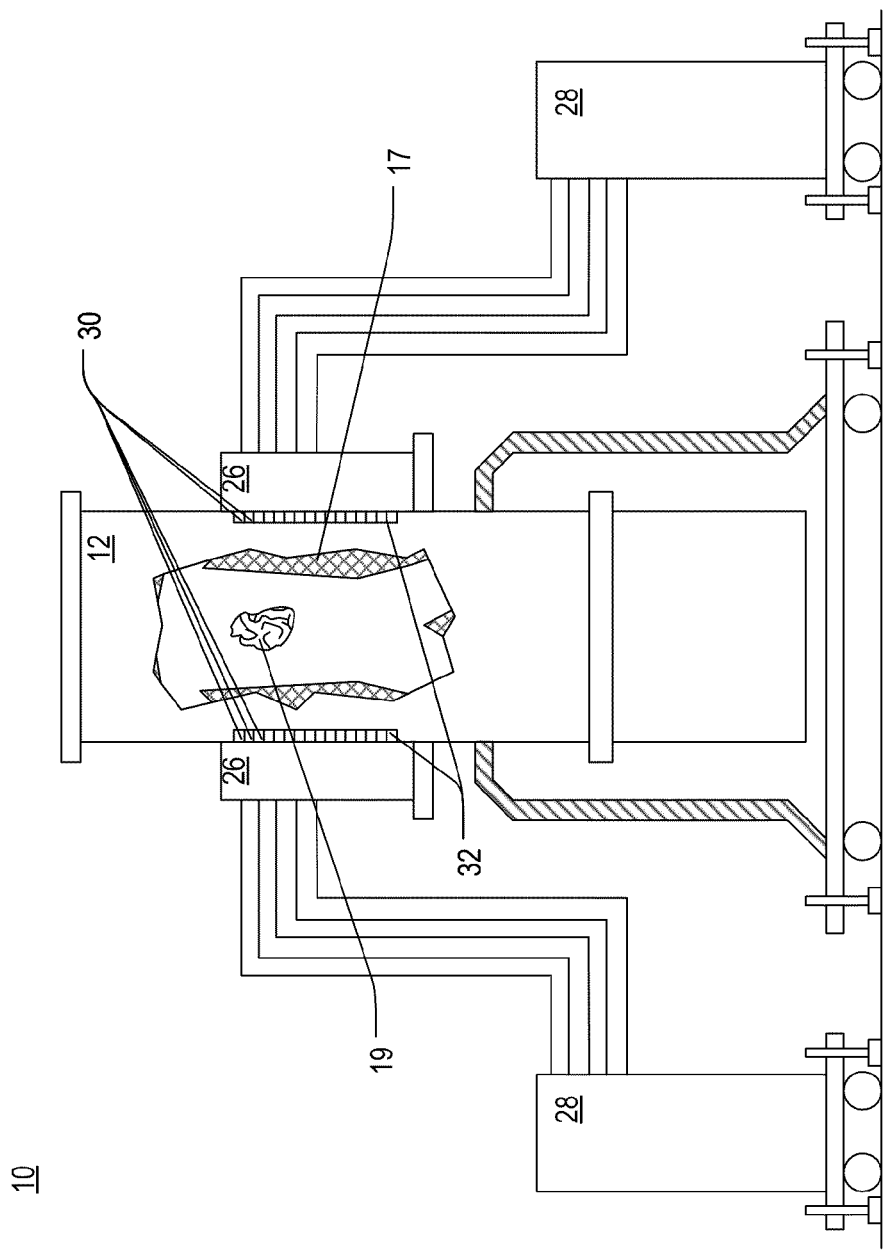
FIG. 2 is a schematic view of an EM field tomographic spectroscopic system for use in one or more preferred embodiments of the present invention.

FIG. 2 is a schematic view of an EM field tomographic spectroscopic system 10 for use in one or more preferred embodiments of the present invention. In particular, the system 10 of FIG. 2 carries out functional imaging of biological tissues. The system 10 might also be used for a non-invasive mapping of electrical excitation of biological tissues 19 using a sensitive (contrast) material (solution or nanoparticles) injected into the biological tissue 19 or in circulation system, characterized by having dielectric properties that are a function of electrical field, generated by biological excited tissue 19, in accordance with the preferred embodiments of the present invention. As illustrated in FIG. 2, the system 10 includes a working or imaging chamber 12, a plurality of "EM field source-detector" clusters 26, an equal number of intermediate frequency ("IF") detector clusters 28, and a control system (not shown in FIG. 2, but illustrated in block diagram form in FIG. 6). Although only two EM field source-detector clusters 26 and two IF detector clusters 28 are shown, it should be clear that a much larger number of each, sometimes denoted herein by N, may (and preferably should) be used.

The imaging chamber 12 is preferably a watertight vessel of sufficient size to accommodate a human body or one or more parts of a human body. For example, the imaging chamber 12 may be i) a helmet-like imaging chamber to image brain disorders (for example acute and chronic stroke, or functional neuroimaging), ii) a cylindrical type (or other shape) chamber for extremities imaging, or iii) a specifically shaped imaging chamber for detection of breast cancer. Therefore an imaging chamber may have different shapes and sizes, the selection of which would be readily apparent to one of ordinary skill in the art. In at least one embodiment, the imaging chamber 12 and its EM field clusters 26, as well as the IF detector clusters 28, may be mounted on carts in order to permit the respective components to be moved if necessary, and the carts may then be locked in place to provide stability.

Figure 3:
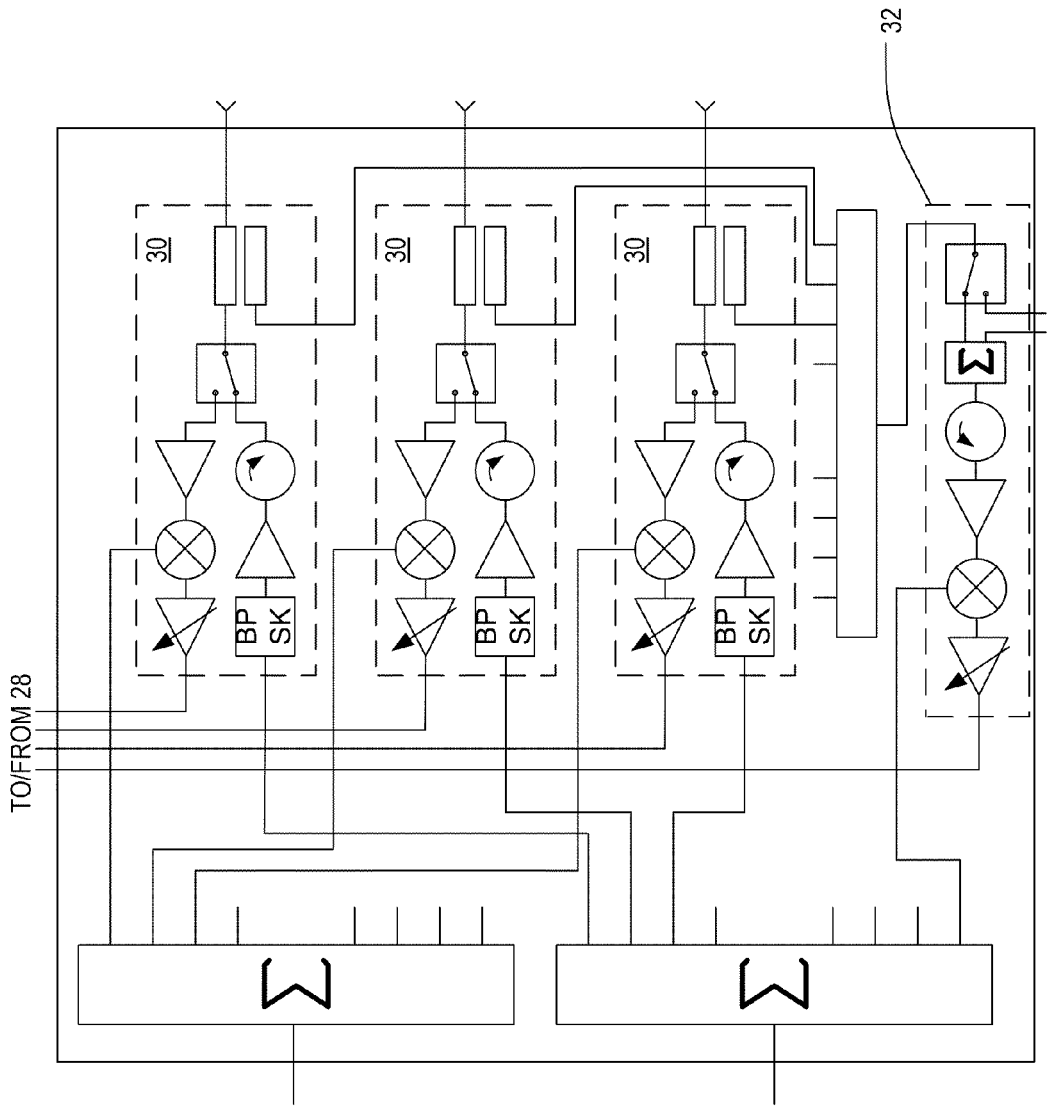
FIG. 3 is a block diagram of one of the N EM field clusters of FIG. 2, wherein the cluster is in its source state.

FIG. 3 is a block diagram of one of the N EM field clusters 26 of FIG. 2, wherein the cluster 26 is in its source state. In a preferred embodiment, each EM field cluster 26 is a main operation unit that may function as an electromagnetic field generator (i.e., an electromagnetic source) or as an electromagnetic field detector, but in other embodiments, the sources and detectors may be separate units. Each cluster 26 has a plurality of source-detector modules 30, one reference channel (sometimes referred to herein as an "R-channel") module 32 and a pair of distribution blocks 64,66, as well as at least two precision attenuators. The number of source-detector modules 30 (three being shown here) in each EM field cluster 26 may sometimes be denoted herein by M. In general, the more source-detector modules 30 that are used, the faster and greater the precision of the system 10. The optimal number of source-detector modules 30 might be when its number corresponds to the number of antennas. In practical cases, issues of manufacturability, convenience and system miniaturization, including mobility, have to be considered.

Figures 4, 5:
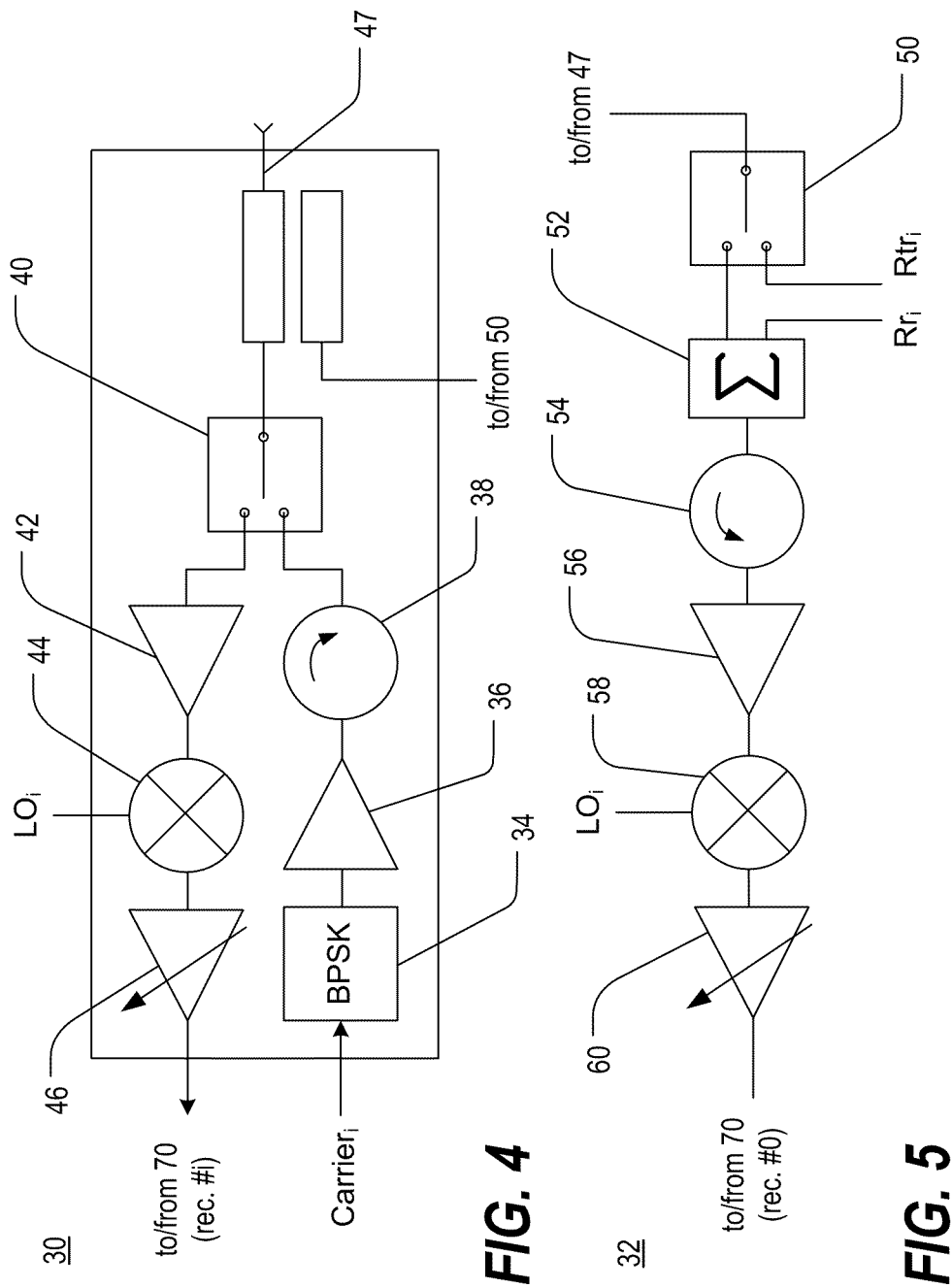
FIG. 4 is a block diagram of one of the M source-detector modules of FIG. 3.
FIG. 5 is a block diagram of the R-channel module of FIG. 3.

FIG. 4 is a block diagram of one of the M source-detector modules 30 of FIG. 3. Each source-detector 30 includes a BPSK modulator 34, a power amplifier 36, a direct uncoupler 38, a switch 40, a low noise amplifier ("LNA") 42, a mixer 44, a programmable gain amplifier ("PGA") 46 and an antenna 48. The switch 40 functions to connect the antenna 48 into the system 10 as an EM source or as an EM detector. When connected as a source (i.e., when the switch 40 is in the lower of the two positions shown in FIG. 4), an input signal provided by one of the distribution blocks 64 (as shown in FIG. 3) is modulated by the BPSK modulator 34, amplified by the amplifier 36 and uncoupled by the direct uncoupler 38 before passing through the switch 40 to the antenna 48. On the other hand, when connected as a detector (i.e., when the switch 40 is in the upper of the two positions shown in FIG. 4), the signals received by the antenna 48 pass through the switch 40 to the LNA 42 where they are amplified and then mixed with a reference signal provided by the second distribution block 66 (as shown in FIG. 3) and then amplified again by the PGA 46.

FIG. 5 is a block diagram of the R-channel module 32 of FIG. 3. As described previously, there are preferably a plurality (M) of source-detector modules 30 in each EM field cluster 26 but only a single R-channel module 32. The R-channel module 32 includes a switch 50, an adder 52, a direct uncoupler 54, an LNA 56, a mixer 58 and a PGA 60. The switch 50 controls whether the R-channel module 32 is in its source state or its detector state. When the R-channel module 32 is in its source state (i.e., when the switch 40 is in the upper of the two positions shown in FIG. 5), output signals from the source-detector modules 30 are passed through the adder 52 and the direct uncoupler 54 and are amplified by the LNA 56 before being mixed with a reference signal and amplified again by the PGA 60. On the other hand, when the R-channel module 32 is in its detector state (i.e., when the switch 40 is in the lower of the two positions shown in FIG. 5), a reference signal is passed straight through to the source-detector modules 30 where it is coupled with the signals received by the respective antennae 48.

Figure 6:
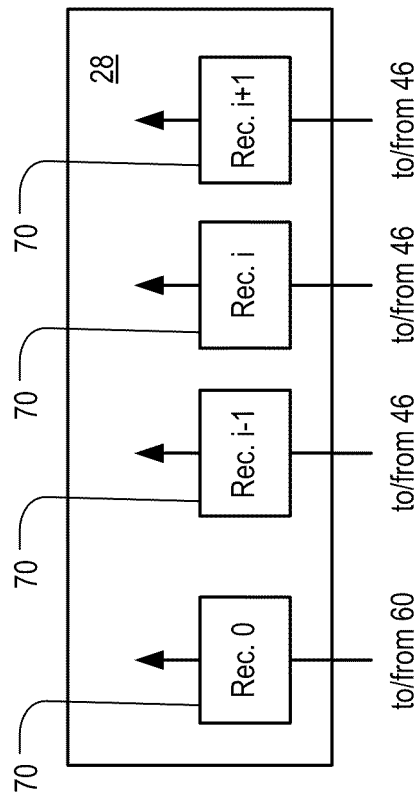
FIG. 6 is a block diagram of one of the IF detector clusters of FIG. 2.

FIG. 6 is a block diagram of one of the N IF detector clusters 28 of FIG. 2. Each IF detector cluster 28 includes a family of M+1 digital correlation detectors 70 for M test signals (one from each of the source-detector modules 30 in a corresponding EM field cluster 26) and one reference channel signal. These digital detectors 70 allow for the informative/working bandwidth of the signal to be selectively passed while restricting other artifacts. Each IF detector cluster 28 also includes a cluster manager, a bus, and a power supply.

Figure 7:
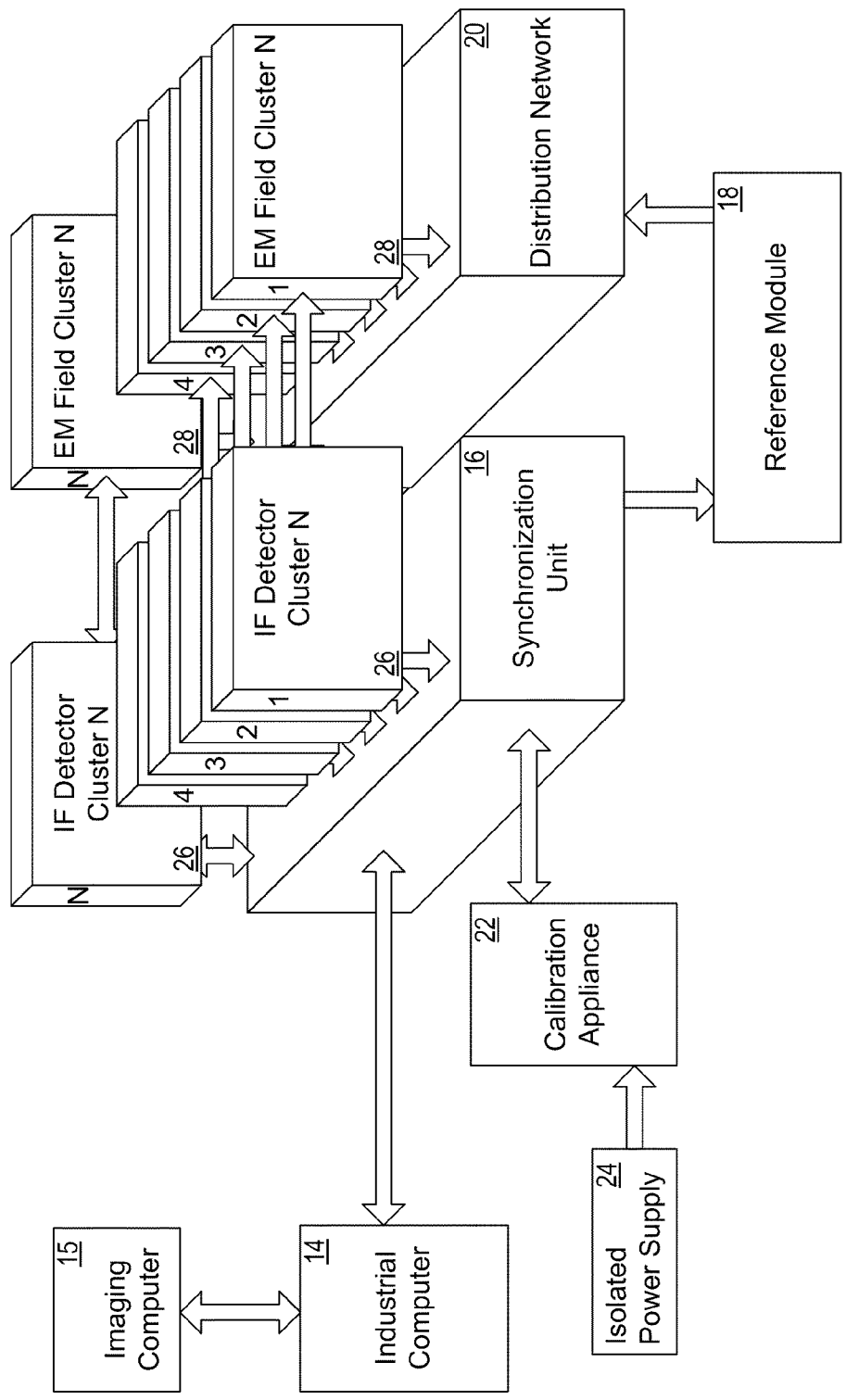
FIG. 7 is a block diagram of the control system for the EM field clusters and IF detector clusters of FIG. 2.

FIG. 7 is a block diagram of the control system for the EM field clusters 26 and IF detector clusters 28 of FIG. 2. The control system includes a control computer 14, an imaging computer 15, a synchronization unit 16, a reference module 18, a distribution network 20, a calibration appliance 22 and a power supply 24. The control computer 14 controls the overall system function, data acquisition, system tuning and calibration and transforms all raw data to the imaging computer 15 for further data inversion and imaging. The control computer 14 may be a conventional personal computer, such as an Intel-based advanced-version PC, with an RS-488.2 port and appropriate software to control the system 10. The synchronization unit 16 is a module that includes a system manager and a system hub. Together, they provide data exchange with the control computer 14 (preferably via a USB 2.0 or Firewire link) and the control managers of the various clusters 26,28, and also provide synchronization of system operations.

The reference module 18 includes two generators, one or more thermostats for temperature stabilization of the function of the reference channels, a BPSK modulator for phase-modulation, power dividers, attenuators and the like. The two generators are precision generators that generate stable CW signals: $Carrier_{ref}$ and $LO_{ref}$. These generators are controlled and tuned by the control computer 14 through an interface. The distribution network 20 is a commutation unit for receiving the carrier and local oscillator reference signals ($Carrier_{ref}$ and $LO_{ref}$) and the Rr and Rtr reference signals ($Rr_{ref}$ and $Rtr_{ref}$) from the reference module 18 and distributing them to each of the EM field clusters 28.

The calibration appliance 22 is used for calibration and fine-tuning of the system 10. The calibration appliance 22 includes calibration source, one or more (preferably two) calibration antennae, precision drives and one or more (preferably three) calibrated phantoms. Calibration antennae and phantoms may be precisely positioned at any point inside the imaging chamber 12 with the help of precision positioning drivers. The isolated power supply 24 provides stable power for the system. One power supply suitable for use with the present invention is a 190/380 3-phase, 10 kVA AC network power supply. Of course, the exact requirements for the power supply 24 may depend upon the power system specifications of the country in which the system 10 is to be operated.

Figure 8:
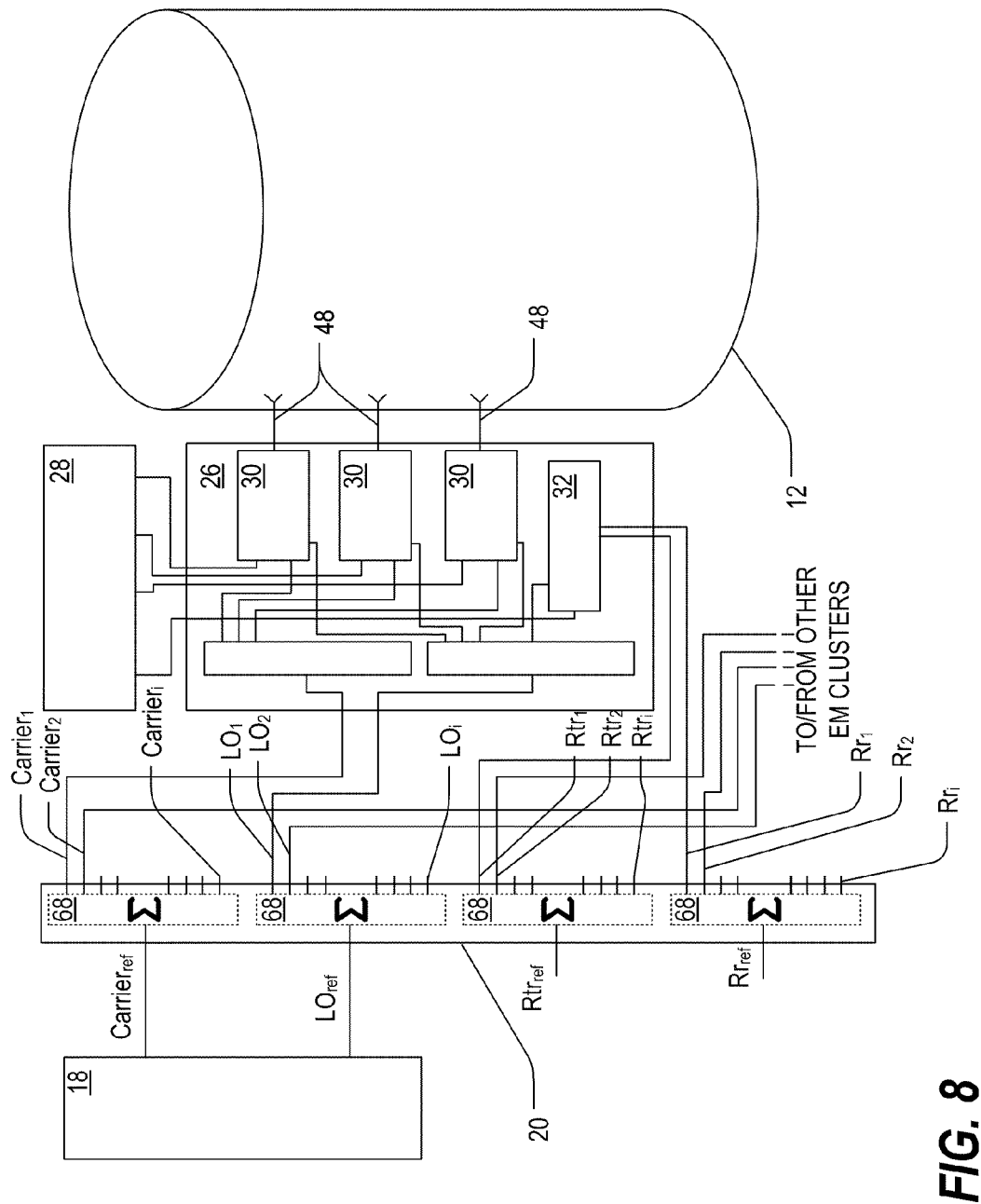
FIG. 8 is a block diagram illustrating the integration of the control system of FIG. 6 with the system of FIG. 2.

FIG. 8 is a block diagram illustrating the integration of the control system of FIG. 6 with the system 10 of FIG. 2. Each EM field cluster 26 is disposed adjacent the imaging chamber 12 such that its antennae 48 are located on or near the surface of the chamber 12. The outputs of the source-detector modules 30 and the R-channel module 32 of each EM field cluster 26 are connected to a corresponding IF detector cluster 28, and each IF detector cluster 28 is connected to both the corresponding EM field cluster 26 and the synchronization unit 16. The inputs of each EM field cluster 26 are connected to the distribution network 20. The distribution network 20 includes at least four distribution blocks 68, which may be 34-channel power dividers, and a system bus for distributing the various reference signals ($Carrier_{ref}$, $LO_{ref}$, $Rr_{ref}$ and $Rtr_{ref}$) to the EM field clusters 26. As illustrated in FIG. 7, one set of the four signals is provided to each EM field cluster 26. These signals are denoted $Carrier_i$, $LO_i$, $Rr_i$ and $Rtr_i$, where the first EM field cluster 26 receives $Carrier_1$, $LO_1$, $Rr_1$ and $Rtr_1$, the second EM field cluster 26 (not separately illustrated) receives $Carrier_2$, $LO_2$, $Rtr_2$ and $Rtr_2$, and so forth. Finally, as described previously, $Carrier_{ref}$ and $LO_{ref}$ are provided to the distribution network 20 by the reference module 18.

In use, the imaging chamber 12 may be filled with one of a variety of solutions or gels 17 selected to match and provide biological compatibility with a biological tissue object 19 to be studied. Suitable solutions 17 may include, but are not limited to, water, salt solutions, sugar solutions, fatty emulsions, alcohol-salt mixed solutions and the like; these solutions may also be used as gel components. The object 19 to be studied may be injected with a sensitive material (solution) (or distributed in the object 19 via the circulation system) whose dielectric properties are a function of the local electrical field generated within the biological excited tissue 19 itself, so that they can be reconstructed via microwave (electromagnetic) tomography. Preferably, the injection materials or solutions are a multi-component media that includes ferroelectrics, such as barium modified strontium titanium oxide, of different grain sizes, which in some embodiments may include spheres, ellipsoids, cylinders, and/or the like. In at least some embodiments, one or more injection materials include complex functionalized nanoparticles (NPs). Specific functionalized NPs might also contain ferromagnetics, biologically compatible shells with specific biological targeting and desired delivery drug. The materials or NPs may also include selected potentiometric dyes, such as merocyanine, rhodamine, cyanine, oxonol and naphthyl styryl, and/or selected potentiometric liquid crystals, such as MBBA, 7CB.

The object under study 19 is positioned inside the imaging chamber 12 and the system 10 is activated. During operation of the system 10, each $Carrier_i$ signal from the signal generator in the reference module 18 is provided to a source-detector module 30, operating in its source mode as shown in FIGS. 3 and 4, where it is modulated using phase-shift modulation (in case of phase characterization) by pseudo-random code in order to distinguish each transmitting antenna 48 or source from the other antennae/sources 48, which are transmitting simultaneously. As described previously, the resultant signal is next amplified before passing through the direct uncoupler 38 to the appropriate source antenna 48. As a result, an incident EM field ("$E_{inc}$"), corresponding to the respective antenna 48 or channel, is formed in the vicinity of the object 19 under study. In addition, part of the signal creating the $E_{inc}$ field is uncoupled and passed to a receiver in the R-channel module 32 (one for each EM field cluster 26). In the R-channel module 32 this signal is mixed with a reference signal $Rr_i$. By subsequently comparing the resultant output with a known signal, $E_{inc}$ may thus be determined precisely as described below.

Figure 9:
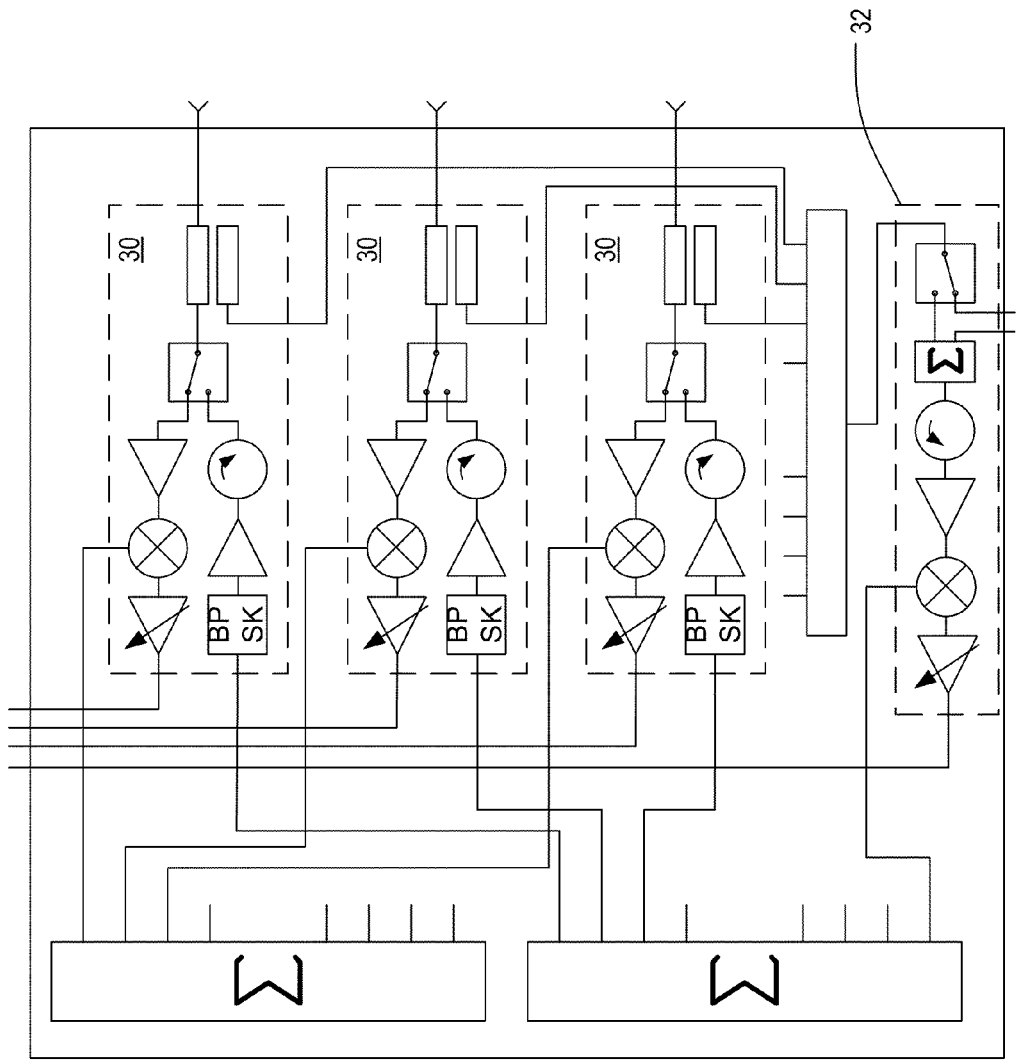
FIG. 9 is a block diagram of the EM field source-detector cluster of FIG. 3, wherein the cluster is in its detector state.

After interacting with the object 19 of interest, each "interferenced" or scattered EM field ("$E_{sct}$") is detected by a corresponding detecting antenna 48 operating in its detector mode. FIG. 9 is a block diagram of the EM field source-detector cluster 26 of FIG. 3, wherein the cluster is in its detector state. The same reference signal $Rr_i$ described in the preceding paragraph is injected into the source-detectors 30 of the EM field cluster 26 (operating in detector mode) immediately downstream from the detecting (receiving) antenna 48. This allows for the R-channel signal $Rr_i$, which is known precisely, to pass through all parts of the detector 30 through which the $E_{sct}$ signal is passed. Therefore, an injection of the R-channel signal into the measuring portions of the source-detectors 30 in both source and detection mode allows for a significant decrease in artifacts caused by temperature and temporary instability of the channel electronics.

Figures 10A, 10B:
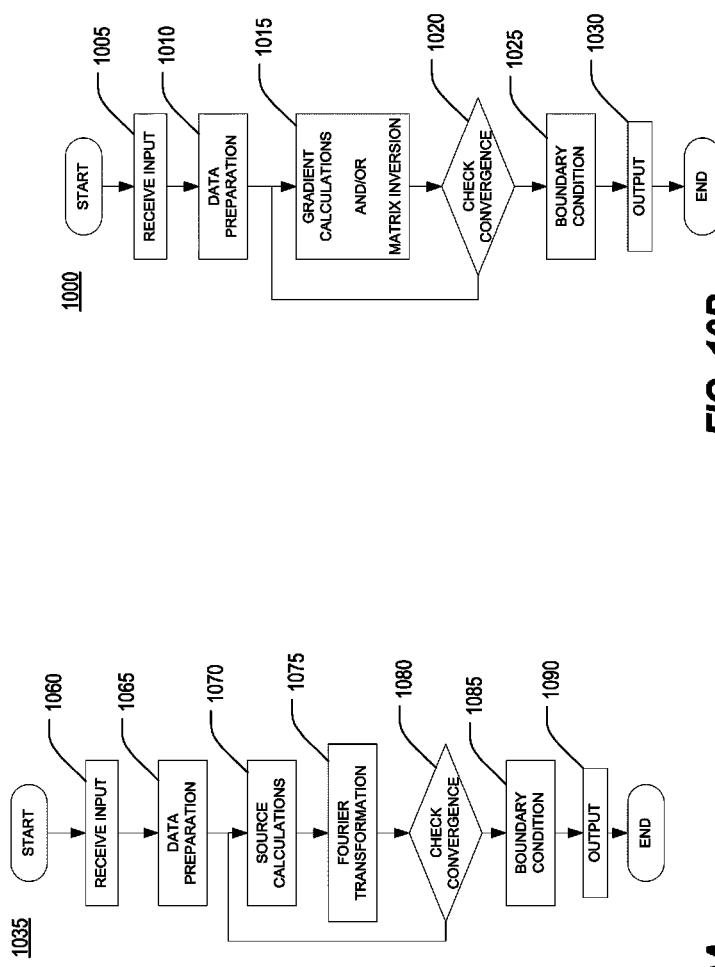
FIG. 10A is a flow diagram of the direct problem solver portion of an image reconstruction process.
FIG. 10B is a flow diagram of the inverse problem solver portion of the image reconstruction process.
Figure 10C:
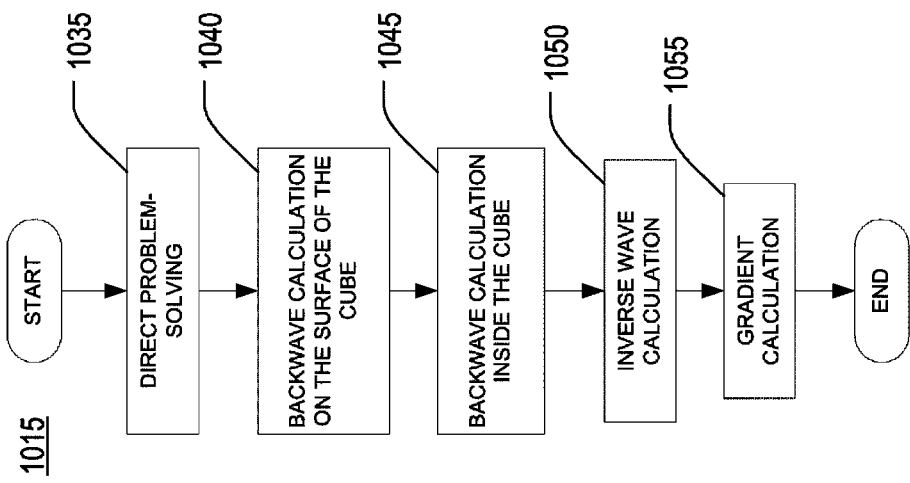
FIG. 10C is a flow diagram of the gradient calculation portion of the image reconstruction process.

The data and other information gathered by the system 10 is provided to the imaging computer 15, which carries out one or more processes to solve an inverse problem of electromagnetic field tomography. The solver might be or include, for example, a non-simplified three-dimensional ("3D") vector solver using Maxwell's equations or a simplified 3D scalar solver or a further simplified 2D scalar solver. FIGS. 10A, 10B and 10C are flowcharts of such process. The method uses an iterative procedure based on either a gradient or a Newton calculation approach or it may use a simplified approach using a Born or Rytov approximation. If a non-approximation approach is used it preferably has one or more of the following features, among others: (i) the method is based on minimization of the difference between model scattered fields and measured scattered fields; (ii) the method uses the Tichonov's type of regularization; (iii) one type of the calculation mesh is used in the method; (iv) one step of the iterative procedure is performed as solving of the two sets of direct problems of the same dimension: modeling of the so-called direct wave and modeling of the inverse wave; (v) both the direct wave and the inverse wave are calculated using nonreflecting or metallic boundary conditions; (vi) both the direct wave and the inverse wave are calculated on the same rectangular mesh; (vii) in order to solve the direct problem a conjugate gradient method ("CGM") might be used; (viii) one step of the CGM uses the sine Fourier transform; and/or (ix) the wave equation for non-uniform media is used to solve the direct problem.

From a mathematical point of view, the methodology utilized in EM field tomography is an inverse problem. It may be formulated in terms of complex dielectric properties $\in$ and/or magnetic properties $\mu$ and electric and magnetic fields –E, H. The basis is a set of the Maxwell's equations as shown in U.S. Pat. No. 7,239,731 ("'731 Patent") equation (1), where E and H represent electrical and magnetic fields, respectively, and all other notations are standard.

It is more practical to rewrite these equations in a form of non-uniform wave equations such as that shown at '731 Patent equation (2), where $$k^2 = (2\pi/\lambda)^2 \in \mu$$

and $\lambda$ is a wavelength in vacuum. The EM field tomographic system could be schematically represented as a chamber with the set of antennae on the surface of the chamber. As described previously, some antennae function as EM field sources while the others function as EM field detectors. It is useful to divide electric field E into incident $E_0$ field and scattered field $E_s$, as shown at '731 Patent equation (3) where j is the number of a particular transmitter or source. The equation (2) can be rewritten in the form shown in '731 Patent equation (4) where $k_0^2$ is a wave number for homogeneous matter and $E_{0j}$ is the field produced by the antenna number j.

An object may be described as a distribution of dielectric permittivity in the imaging domain.

A receiver antenna and receiver electronic unit detects the complex signal (for example, its amplitude and phase), which reflects both incident and scattered fields.

In order to solve equation (4) we need to use some boundary conditions on the bound of a calculation domain. Both nonreflecting and reflecting (metallic) boundary conditions may be used on the domain bounds. An interaction of the electromagnetic fields with antennae is solved as a separate problem.

Antenna Modeling.

In practical applications, the value of incident fields is the important part of a reconstruction algorithm. Using the FDTD method it has been found that for a rectangular waveguide transmitter (of an optional antenna type), the field distribution can be described as the vector Kirchhoff integral with a cosine distribution of electric field on the edge of the antenna, as shown in '731 Patent equation (5). The equation (5) shows good agreement with the experimental results. The same type of antenna may be used as a receiver. To describe the process of a signal recording the reciprocity principle may be used. It could provide different expressions for recorded signal. Two of them are used in our calculations. First, $S_{ij}$ may be found using '731 Patent Equation (6), where $S_{ij}$ is the signal received by antenna number i in the situation where antenna number j works as a transmitter or source, $C_1$ is a constant, $E_i$ is an electrical field distribution produced by the detecting antenna, $E_j$ is an electrical field distribution produced by the source antenna, $\Delta \in$ is dielectric permittivity distribution in the object, and the integral is taken in the domain V where the object is located. The equation (6) is used in the inverse problem solution shown at '731 Patent equation (7) where the integral is taken over the surface of the domain.

Direct Problem Solver

In order to solve direct problems a conjugate gradient method may be used with a preconditioner. In order to do that, equation (4) may be rewritten in the form shown in '731 Patent equation (8), where $k_{av}$ is an average value of k. The preconditioner operator can be constructed as a first step of the iterative process shown at '731 Patent equation (9). Taking into account the fact that the left side of equation (8) is an expression with constant coefficient, equation (9) can be solved at step 1075 using sine-type Fourier transform for the case with zero boundary conditions on the bound of calculation domain. Then R. A. James's method (originally invented for static problems, but subsequently developed for electromagnetic problems) is applied to make boundary conditions nonreflected. This technique creates a very robust and effective method. Computational experiments show that the iterative process appears to work with any reasonable contrasts and provides nonreflecting conditions with very high accuracy. Using a sine-type Fourier transform at step 1075 can make calculations eight times faster than with the regular Fourier approach.

FIG. 10A is a flow diagram of the direct problem solver portion 1035 of the image reconstruction process. The direct solver 1035 is used only for inverse problem solving. The input data in this case is the dielectric properties distribution in the form of a 3D array, which is received at step 1060. For the first step of the iteration, this input data is received from external input, while in subsequent iterations it is received from the previous iteration. Next to occur, at step 1065, is the preparation of the parameters and arrays, which do not change during the direct problem solving process: the wave number, the computational grids, and the Green function for the uniform space. After that, the iterative procedure of the conjugate gradients takes place at steps 1070 and 1080. First, the source member of equation (4) is calculated at step 1070. Then, every step of the conjugate gradient method requires fast Fourier transforms of the source functions, as shown at step 1075. In order to stop iterations the convergence of the process is checked at step 1080. Once the iterative procedure is finished, the non-reflecting boundary conditions have to be implemented at step 1085. Finally, the output of the process 1035 is created at step 1090. The output comprises arrays containing the electric fields inside of the computational domain and signals on the receivers for all transmitter positions.

Inverse Problem Solver.

In order to solve the inverse problem in microwave (electromagnetic) tomography the gradient or Newton method may be applied. In the case of a three-dimensional vector in cylindrical geometry this method needs significant modifications when compared with two-dimensional and scalar cases. In general the inverse problem in EM field tomography can be formulated as a minimization problem as shown at '731 Patent equation (10), where $S_{ij}^{theor}$ are the theoretical values of the signal, $S_{ij}^{exper}$ are experimental values of the signal, and the last term is the Tichonov's regularization functional.

An important point of any minimization procedure for gradient based methods is the method of a gradient calculation itself. It was proven that the gradient of functional in our case is set forth at '731 Patent equation (11) where $E_j$ and $G_{ij}$ are solutions of '731 Patent equations (12) and (13). Functions $F_j$ and $P_{ij}$ describe the field patterns for antennae 48 being used as sources and detectors, respectively.

Direct computation using the equation (11) is very time consuming even in the 2D case and cannot be effectively applied in the 3D case. The reason is that every step requires N×M number of direct problems to be solved, where N is the number of transmitters, and M is the number of receivers. It was shown in previous "scalar" work, and can be generalized in the vector case, that the function shown at '731 Patent equation (14) can be the solution of '731 Patent equation (15). This makes it necessary to solve only two direct problems on each iterative step.

The calculation of the sum in the right side of equation (15) continues to be a difficult problem, because it requires summation on all receivers for all cells of the computational mesh. In order to overcome this obstacle, a two-step procedure may be applied. First, '731 Patent equation (16) may be calculated on the surface of the computational domain. This needs significantly less computational effort compared to the calculation of the right part of equation (15). Second, '731 Patent equation (17) may be solved with those boundary conditions. Equation (17) is the equation with constant coefficients and can be easily solved using sine-type FFT.

Finally, one step of the gradient method procedure requires solving two direct problems (equations (12) and (15)) plus one equation (equation (17)) with constant coefficients. In general this procedure looks to be the fastest known in literature.

One step of the iterative procedure can be implemented as shown at '731 Patent equation (18), where an iterative step is chosen in a trial method. The limitations on the upper and lower bounds of the values of the dielectric properties and the values of the dielectric properties on the bound of the object are applied in this step.

FIG. 10B is a flow diagram of the inverse problem solver portion 1000 of the image reconstruction process when a gradient-based method and/or Newton-based method is in use. At step 1005, the input data is received. The input data for the inverse problem solver 1000 includes physical and geometrical parameters of the computational process: the sixes of the computational domain, the working frequency, the maximum number of iterations and the signals from the antennae 48. Next to occur, at step 1010, is the preparation of the parameters and arrays, which do not change during the inverse problem solving iteration process These parameters may include, but are not limited to, the wave number, the computational grids, and the Green function for the uniform space. After that, the iterative procedure of calculating the gradient of the residual function (equation (11)) and/or matrix inversion (for Newton based methods) takes place at steps 1015. In order to stop iterations the convergence of the process is checked at step 1020. This involves comparing the value of the residual error with the estimated experimental error. Once the iterative procedure is finished, the non-reflecting boundary conditions have to be implemented at step 1025. Finally, the output of the process 1000 is created at step 1030. The output comprises the dielectric properties distribution in the form of a 2D or 3D array.

FIG. 10C is a flow diagram of the gradient calculation portion 1015 of the image reconstruction process. The direct wave is calculated at step 1035 according to equation (12), followed at step 1040 by the calculation according to equation (16) of the source for back-propagating wave on the bounds of the computational domain. Then, at step 1045, the source of the back-propagating wave is calculated in the volume of the computational domain according to equation (17), and the back-propagating wave is calculated by solving equation (13) at step 1050. Finally, the gradient is calculated according to equation (11) at step 1055.

The image reconstruction algorithm of this invention includes a number of benefits. For example, using the nonreflecting boundary conditions plus sine-type FFT makes the direct problem solver of the invention the most effective one. Further, the proposed way to calculate the so-called back wave (equations (15), (16), (17)) allows working in real 3D multi antenna configuration. In addition, the method of signal calculation (equation (7)) is distinguished from any others and allows simulating the work of each antenna with high precision, and the mathematical algorithm itself is essentially parallel, which is particularly advantageous for parallel computing.

Figure 11:
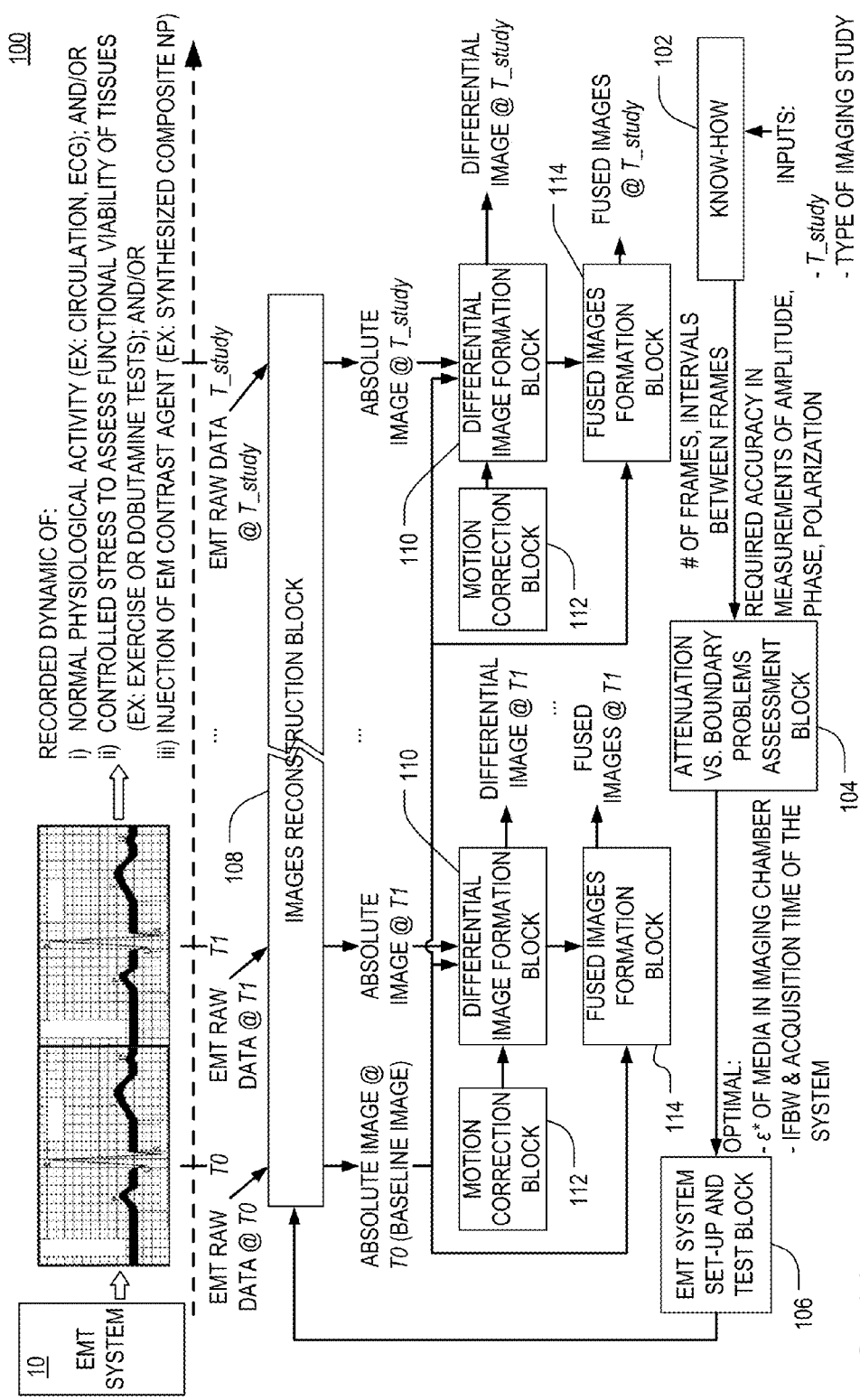
FIG. 11 is a schematic diagram illustrating the use of the system and methods of FIGS. 2-10 in a 4D EMT differential (dynamic) fused imaging system in accordance with one or more preferred embodiments of the present invention.

FIG. 11 is a schematic diagram illustrating the use of the system 10 and methods of FIGS. 2-10 in a 4D EMT differential (dynamic) fused imaging system 100 in accordance with one or more preferred embodiments of the present invention. As used herein, $\in^*$ means a complex number, unless otherwise indicated. The system includes a "know-how block" 102, an "attenuation vs. boundary problems assessment block" 104, "an EMT system set-up and test block" 106, an "images reconstruction block" 108, a "differential image formation block" 110, a "motion correction block" 112, and a "fused images formation block" 114.

As shown in the lower right-hand corner, two important inputs into the method and system are the type of imaging study and the time duration of the study (T_study). The type of imaging study may, for example, be i) a dynamic study of normal physiological activity within soft tissue of extremity or myocardial tissue or brain tissue, ii) a controlled stress study to assess a functional viability of tissues (for example myocardium or muscle tissue) during physical stress (exercise) or pharmacologically induced stress (for example using dobutamine as per already approved clinical procedure), iii) an injection of electromagnetic contrast agent(s) (e.g., synthesized composite functional nanoparticles), or the like, or a combination of the foregoing. The time duration of the study (T_study) may be input, for example, in units of seconds or a number of cycles of physiological activity (for example, cardiac cycles).

Based on the input, the system calculates, as represented by the "know-how" block 102, various desired system parameters. These preferably include the required timely resolution (timely intervals between each EMT acquisition cycle (frame)), the number of frames to be acquired by the system, the required accuracy of measurements in amplitude, the required accuracy of measurements in phase, and the required accuracy of measurements in polarization (if needed).

Using this information, the "attenuation vs. boundary problems assessment block" 104 calculates i) optimal dielectric properties ($\in^*_0=\in'_0+j\in''_0$) of matching solution (solution to be filled in the imaging chamber), mainly by optimizing an attenuation component ($\in''_0$), and ii) IFBW of the system based on required timely resolution and number of channels of the system to be acquired. Then the matching solution is prepared by mixing water, alcohol and salt or other components as described earlier at an appropriate concentration to match desired dielectric properties ($\in^*_0=\in'_0+j\in''_0$). The working or imaging chamber 12 may then be filled with such solution.

Using the "EMT system set-up and test block" 106, the system 100, including the EMT system 10, is set up and initialized and, with the solution in place, a test may be conducted using an "empty" imaging chamber—i.e., with the chamber 12 filled with matching solution but with no object 19 under study or solution or gel 17 inside. This allows for assurance that the desired system parameters are met.

When the system 100 is ready, the object 19 under study is placed into the imaging chamber 12, along with the solution or gel 17, and full set EMT data (frames) are acquired as described above at each time T0, T1 . . . T_study. The raw EMT data at each time frame comes into an image reconstruction block 108 to calculate an absolute anatomical image at each time frame T0, T1 . . . T_study. The absolute anatomical image that is determined at time T0, which may sometimes be referred to herein as a "BaseLine image," is used to calculate a differential image and fused images at all further frames T1 . . . T_study. For frame T0, the starting point (initial distribution of dielectric properties within an imaging domain) for an iterative image reconstruction procedure may be a homogeneous distribution of matching solution $\in^*_0=\in'_0+j\in''_0$ within an imaging domain. For all other frames (T1 . . . T_study), the starting point may be a homogeneous distribution of matching solution $\in^*_0=\in'_0+j\in''_0$ within an imaging domain (a BaseLine image ($\in^*_{frame\ T0}$)), or alternatively, the starting point may be a reconstructed image from previous frame. In other words, a BaseLine image ($\in^*_{frame\ T0}$), which is a reconstructed distribution of dielectric properties at time T0, can be used as a starting point for image reconstruction at other time points (frames) T1 . . . T_study, or alternatively an image reconstructed at time Ti ($\in^*_{frame\ Ti}$) can be used as a starting point for image reconstruction at frames i+1, i+2 etc. This significantly accelerates an image reconstruction procedure by decreasing a required number of iterations.

The "differential image formation block" 110 calculates differential images between the initial frame T0 and the current frame Ti as follows:

$$\in^*\text{diff}=(\in^*_{frame\ Ti}-\in^*_{frame\ T0})/\in^*_{frame\ T0}\times 100[\%]$$

It is strongly preferred that the reconstructed images at time T0 and Ti are to be motion free. In spite of a very short acquisition time (preferably on the order of a dozen milliseconds or less), motion correction might be required. This may be conducted in the "motion correction block" 112.

A fused image at each time frame Ti may be obtained via the "fused images formation block" 114. In one implementation, a background image, representing the absolute anatomical image of the biological object 19, is produced using a gray palette, and a time-differential image, produced using a color palette, is superimposed over the background image. In the absolute anatomical image, bony areas having low dielectric properties may be rendered using darker shades of gray while soft tissue areas may be rendered using lighter shades of gray. In the time-differential image, which reflects physiological activity or interventions during the study, the degree of such changes may be rendered, as represented in the color bar, as a percentile of changes. Simple examples of such fused images, obtained during preliminary experiments using the foregoing systems and methods described above, are described below.

Examples: Swine Medial Foreleg

Figure 12:
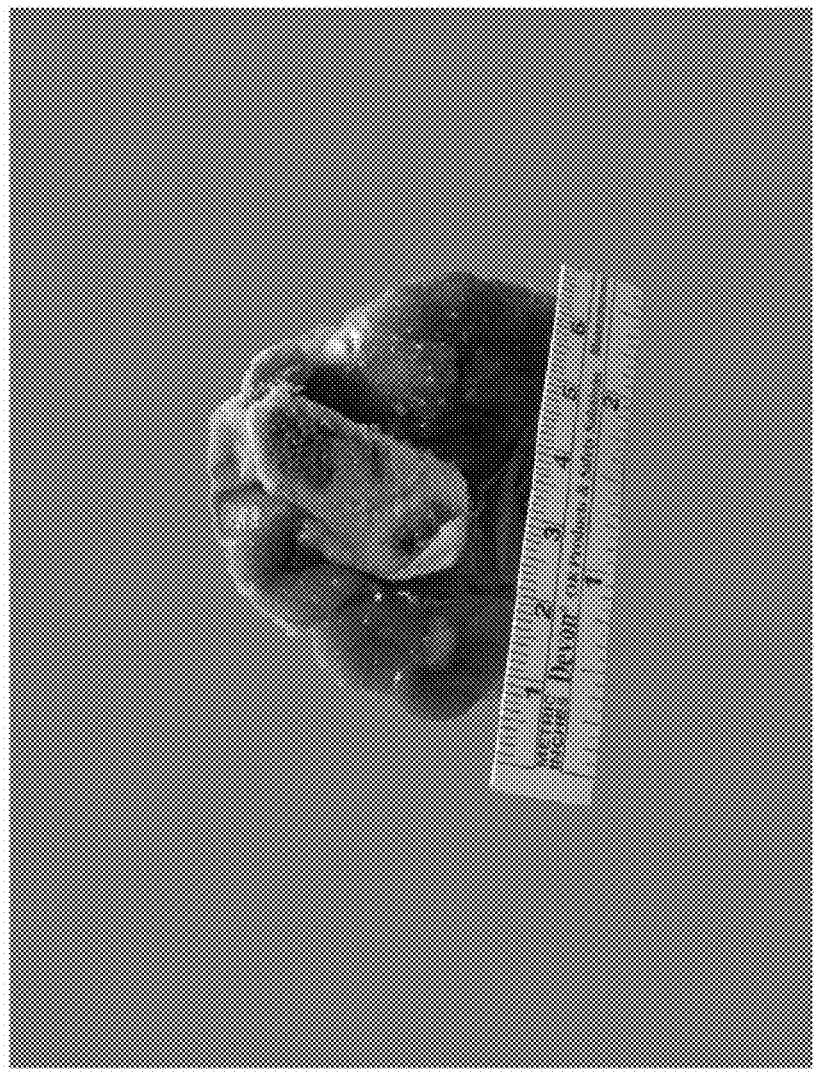
FIG. 12 is a photograph of an anatomical cross section of a swine medial foreleg as utilized in illustrative EMT imaging experiments.

In order to validate the methodology described herein, experiments were conducted using a portion of a swine medial foreleg. FIG. 12 is a photograph of an anatomical cross section of a swine medial foreleg as utilized in such experiments.

One set of experiments focused on circulatory-related changes, including systolic versus diastolic and reperfusion versus occlusion. FIGS. 13A-13B and FIGS. 14A-14B are imaging results presented as fused images, in simplified 2D geometry, of circulatory-related changes for the systolic versus diastolic case and of circulatory-related changes for the reperfusion versus occlusion case, respectively. In each pair of imaging results, the top imaging result presents a fused image of $\in'$ and the bottom imaging result presents a fused image of $\in''$. A 2D Newton iterative method was used for image reconstruction. The reconstructed absolute anatomical images (background image, presented in gray palette) correlate well with anatomy (as represented in FIG. 2) and clearly reveal the bony area having low dielectric properties (dark shades of gray) and the soft tissue component having higher dielectric properties (lighter shades of gray). Although in these experiments the reconstructed values of dielectric properties are not within a range of expected/tabulated properties of the tissues, at least one other study has demonstrated that it is possible to more precisely reconstruct the absolute values of the dielectric properties even with a 5-10% noise figure. The problem is generally one of complexity and optimization.

Figure 13A:
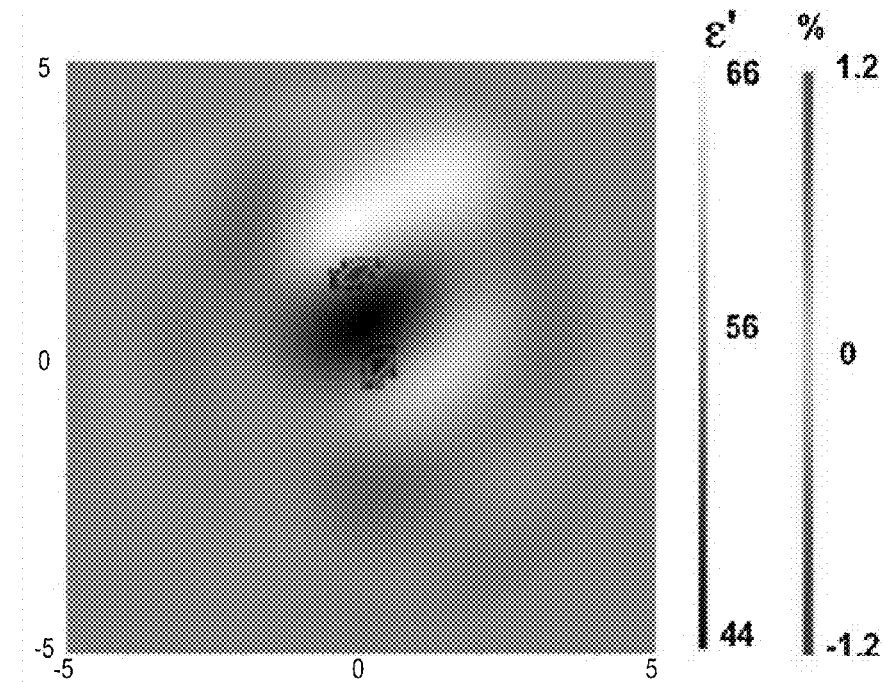
FIGS. 13A and 13B are imaging results presented as fused images, in simplified 2D geometry, of circulatory-related changes for the systolic versus diastolic case.
Figure 13B:
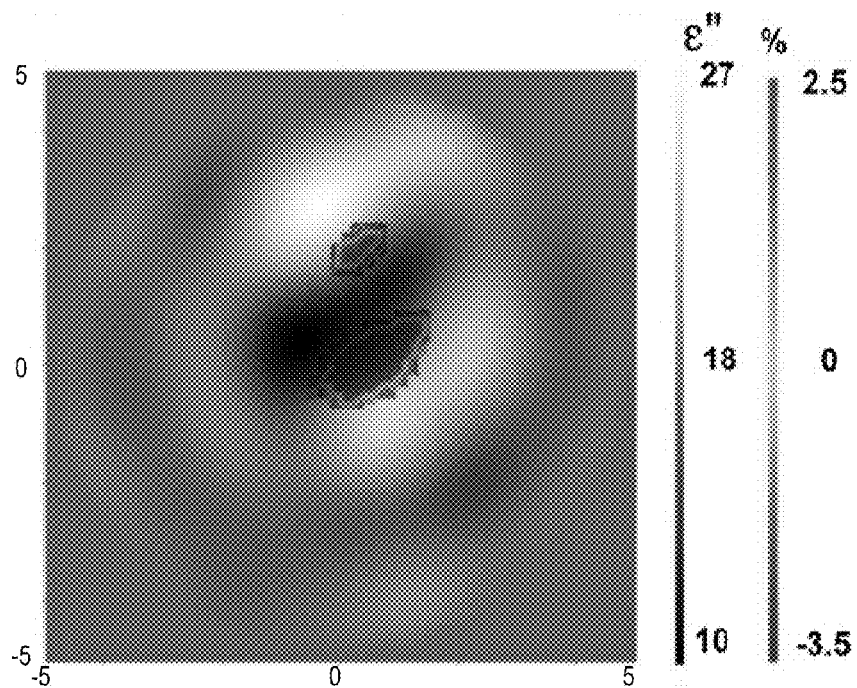
Figure 14A:
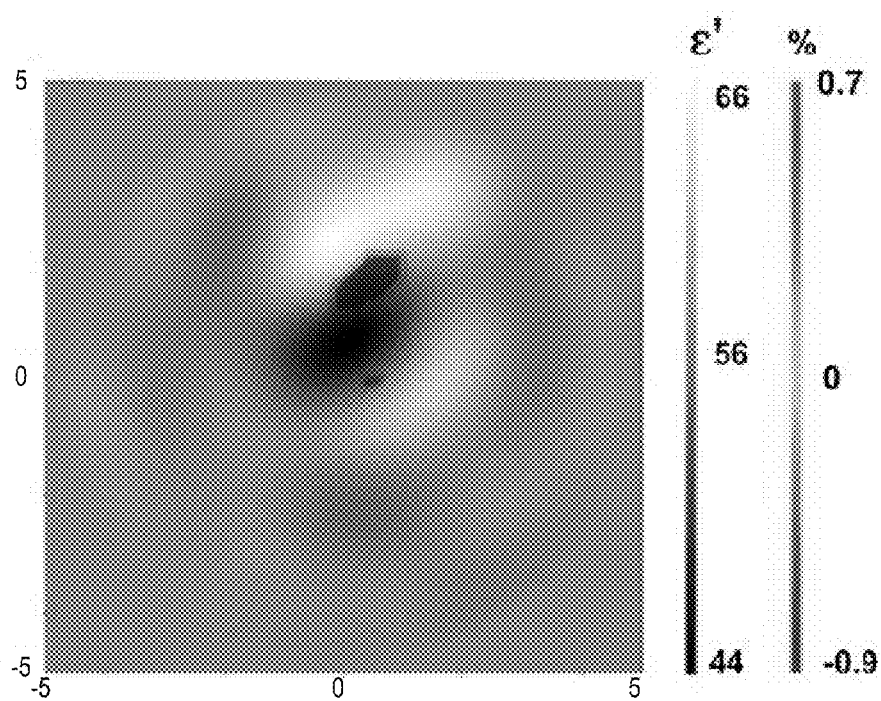
FIGS. 14A and 14B are imaging results presented as fused images, in simplified 2D geometry, of circulatory-related changes for the reperfusion versus occlusion case.
Figure 14B:
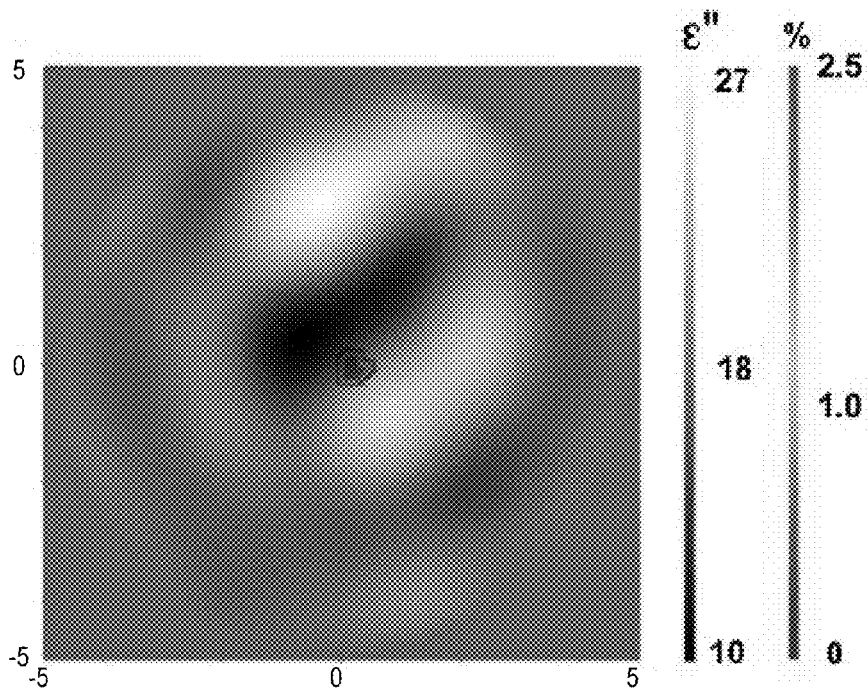
Figure 15A:
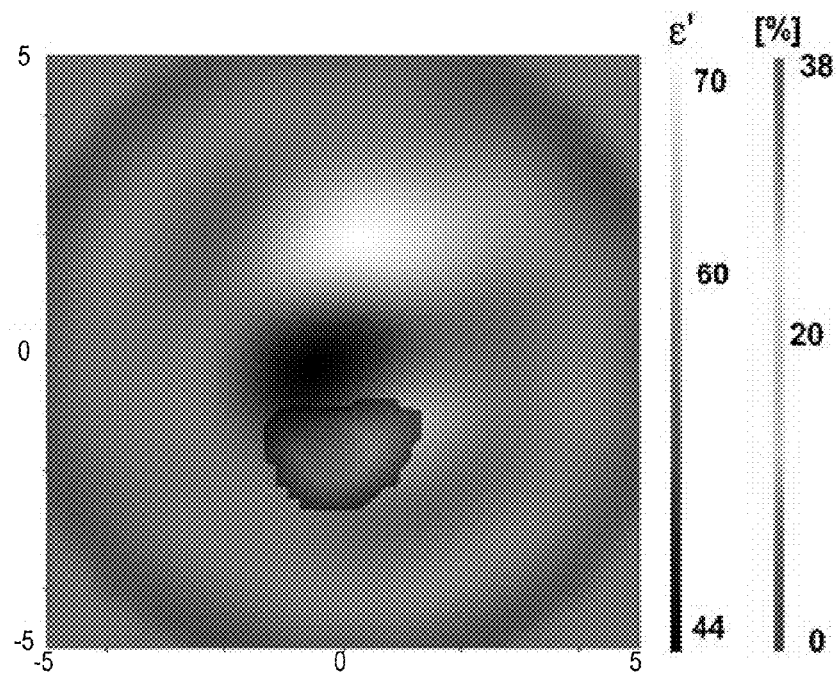
FIGS. 15A and 15B are imaging results presented as fused images, in simplified 2D geometry, of compartmental injury as determined five minutes (+5) after developing the injury, wherein the operational frequency was 1.05 Ghz.
Figure 15B:
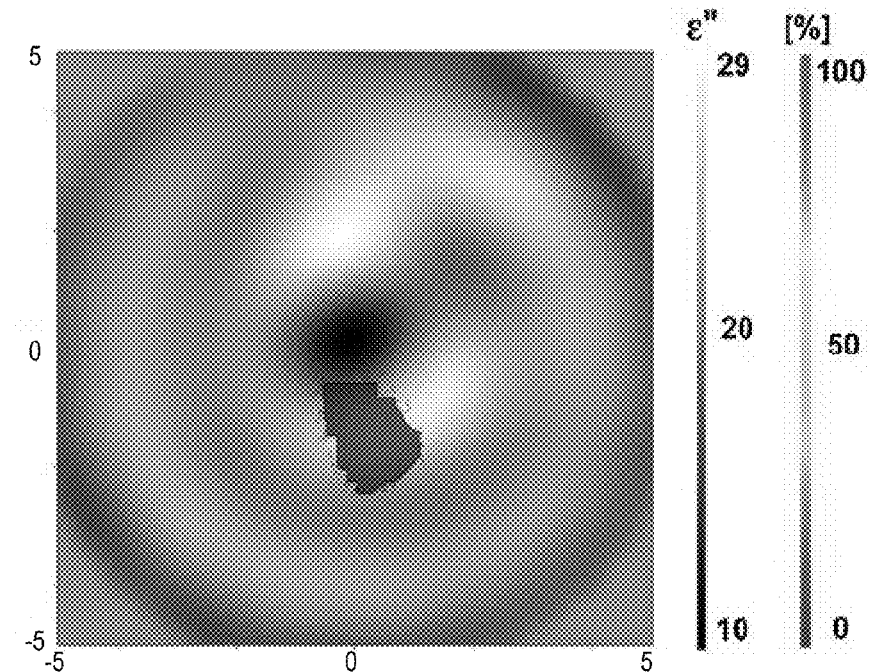
Figure 16A:
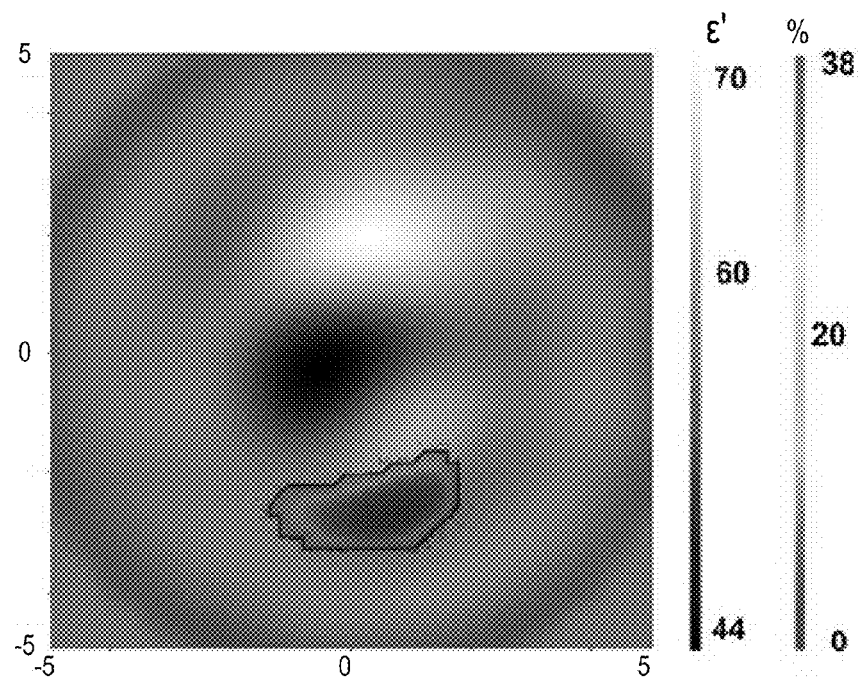
FIGS. 16A and 16B are imaging results presented as fused images, in simplified 2D geometry, of compartmental injury as determined sixteen minutes (+16) after developing the injury, wherein the operational frequency was 1.05 Ghz.
Figure 16B:
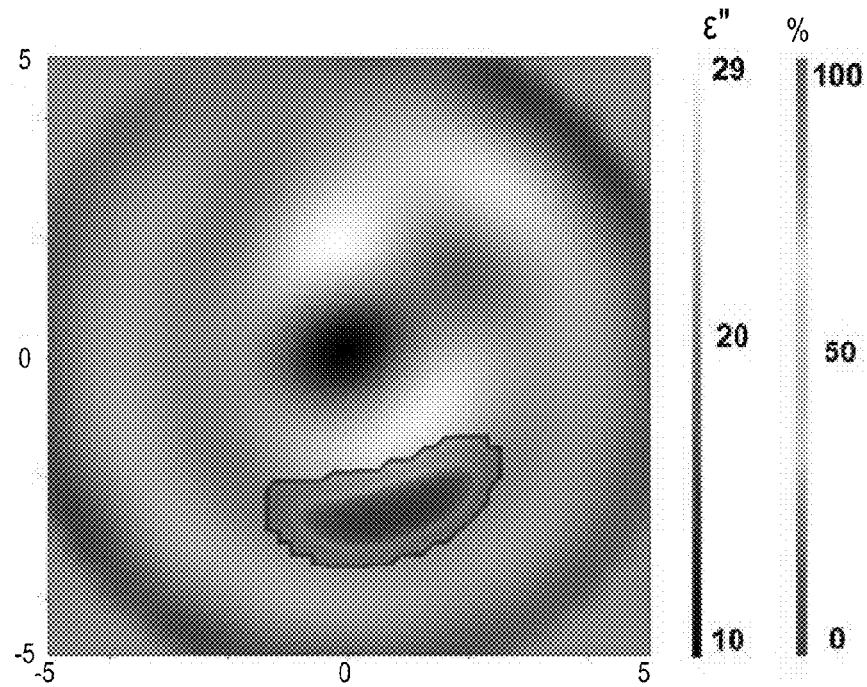
Figure 17A:
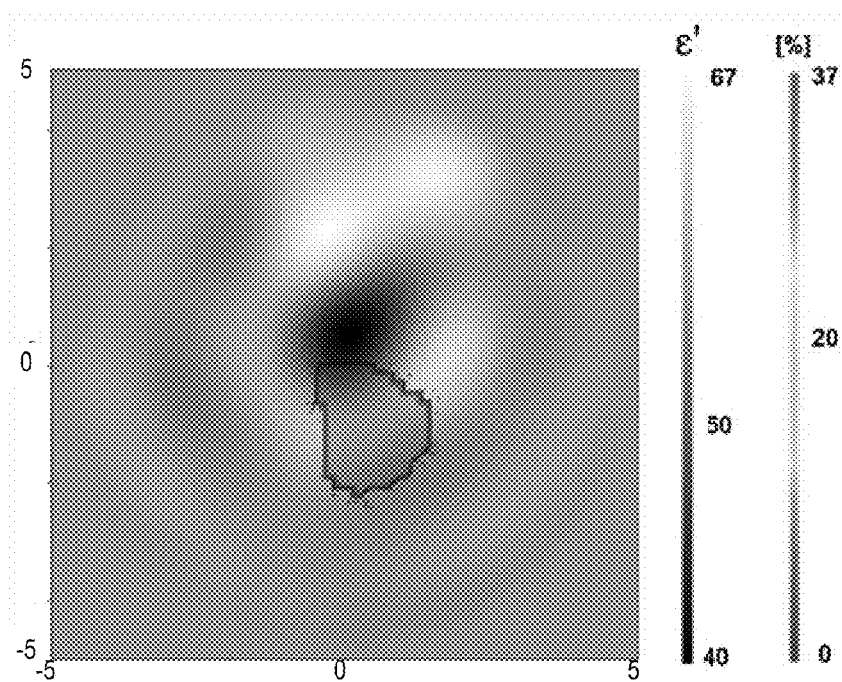
FIGS. 17A and 17B are imaging results presented as fused images, in simplified 2D geometry, of compartmental injury as determined five minutes (+5) after developing the injury, wherein the operational frequency was 1.5 Ghz.
Figure 17B:
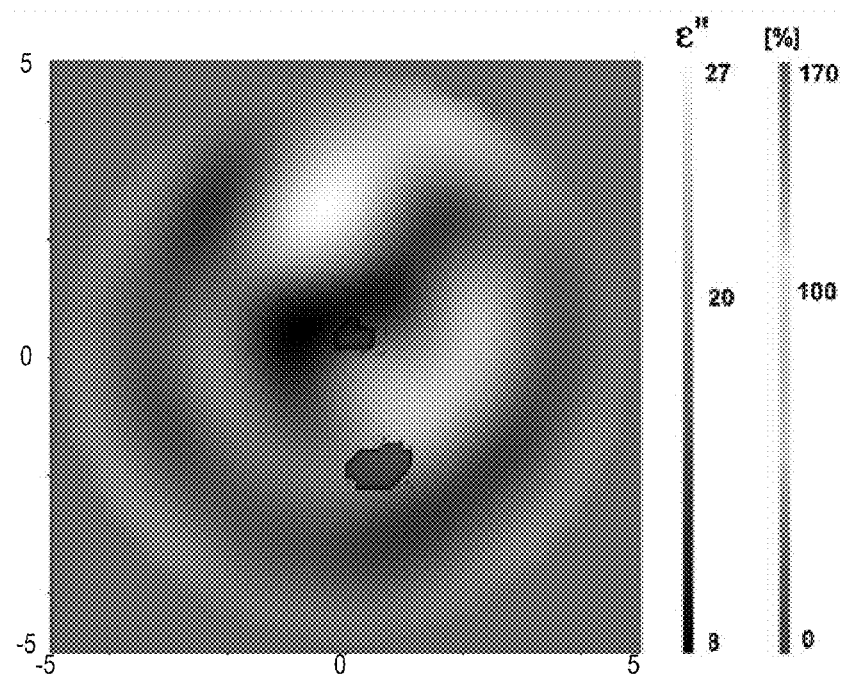
Figure 18A:
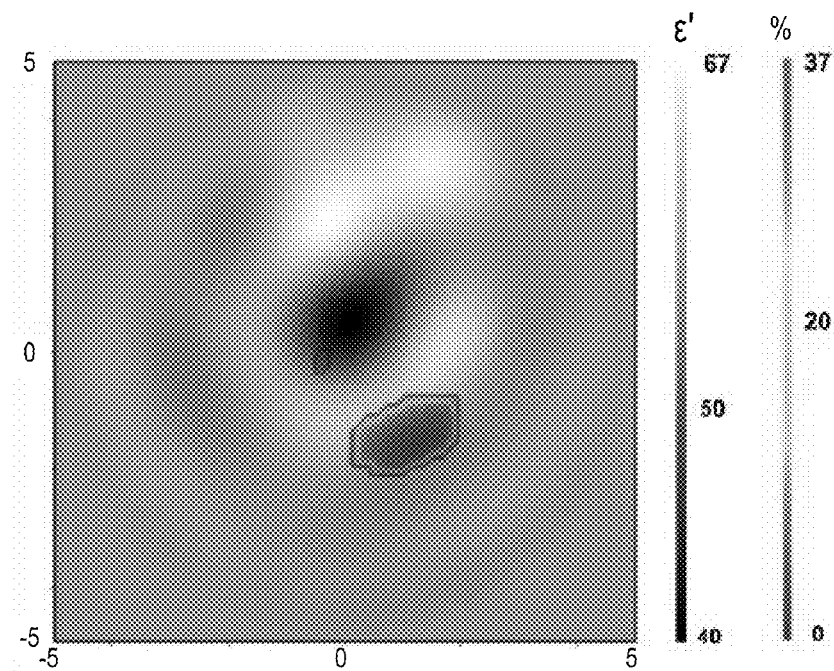
FIGS. 18A and 18B are imaging results presented as fused images, in simplified 2D geometry, of compartmental injury as determined sixteen minutes (+16) after developing the injury, wherein the operational frequency was 1.5 Ghz.
Figure 18B:
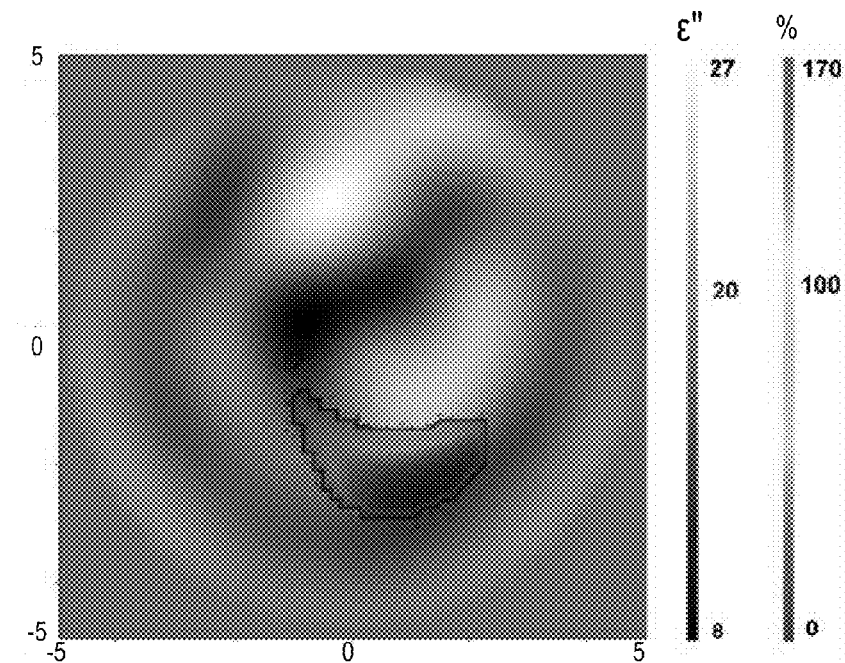

In each fused image, the colored area indicates the degree of physiological change, resulting from interventions to soft tissue, expressed as a percentage change. In FIGS. 13A-13B, which correspond to circulatory-related changes for the systolic versus diastolic case, this is calculated as ($\in$_systolic-$\in$_diastolic)/$\in$_diastolic (expressed as a percentage), while in FIGS. 14A-14B, which correspond to circulatory-related changes for the reperfusion versus occlusion case, this is calculated as ($\in$_reperfusion-$\in$_occlusion)/$\in$_occlusion (expressed as a percentage). The existence of these changes in $\in$' and $\in$", which stem from physiological changes resulting from interventions to soft tissue, has been previously established. In at least one study conducted by one or more of the present inventors, there were differences in measured EM fields of up to 10-20% in amplitude and 4-6° in phase, detected only on two to three receivers of the maximum thirteen receivers within the experimental system (for a particular configuration of transmitters/receivers). Improved results may be expected if more receivers per measurement domain were available.

Time-differential images fused with anatomical ones as shown in FIGS. 13A-13B and FIGS. 14A-14B indicate circulatory-related changes while they are consistent with the anatomical location of blood vessels. The percentage of changes was small, within the range of 1% in $\in$' and 2-3% in $\in$". In this regard, it will be appreciated that within microwave tomography the averaged dielectric properties over a certain volume are reconstructed. In this case, it includes blood vessels together with a portion of skeletal muscle. In early non-imaging experiments and computer simulations, the present inventors have suggested that in spite of the fact that MWT technology is in its early development stage, it is estimated that this technology is able to reconstruct about 3-5% change in overall cross-sectional blood flow. Further studies may be executed to ascertain the relationship in between changes in extremity blood flow and the values of reconstructed differential images. This will allow for direct applications of this novel imaging modality in clinical settings.

Another set of experiments focused on the development of simulated compartment syndrome in the swine extremity. In one experiment, the MWT system 100 was operated at a frequency of 1.05 Ghz, while in another the system 100 was operated at a frequency of 1.5 GHz. FIGS. 15A-15B and FIGS. 16A-16B are imaging results presented as fused images, in simplified 2D geometry, of compartmental injury as determined five minutes (+5) and sixteen minutes (+16), respectively, after developing the injury, wherein the operational frequency was 1.05 Ghz. FIGS. 17A-17B and FIGS. 18A-18B are imaging results presented as fused images, in simplified 2D geometry, of compartmental injury as determined five minutes (+5) and sixteen minutes (+16), respectively, after developing the injury, wherein the operational frequency was 1.5 Ghz. In each pair of imaging results, the top imaging result presents a fused image of $\in$" and the bottom imaging result presents a fused image of $\in$". A 2D Newton iterative method was used for image reconstruction. As with the experiments involving circulatory-related changes, the reconstructed absolute anatomical images (background image, presented in gray palette) correlate well with anatomy (as represented in FIG. 2) and clearly reveal the bony area having low dielectric properties (dark shades of gray) and the soft tissue component having higher dielectric properties (lighter shades of gray).

In each fused image, the colored area indicates the degree of physiological change, associated with the development of a simulated compartment syndrome, expressed as a percentage change. The change is calculated as are ($\in$_+xmin of comp injury-$\in$_baseline)/$\in$_baseline (expressed as a percentage). As with circulatory-related changes, the existence of these changes in $\in$' and $\in$" has been previously established. However, the overall differences associated with the development of a simulated compartment syndrome in an animal extremity are much more significant: up to six times in amplitude and up to 150° in phase at +16 min of the development of the syndrome. This suggests confident image reconstruction revealing the location and degree of an injury within the extremity soft tissue.

Time-differential images fused with anatomical ones as shown in FIGS. 15-18 indicate changes in the extremity associated with the development of a simulated compartment syndrome and are consistent with the anatomical location of intervention. More particularly, the images show that there was an anticipated accumulation of extra fluid suggested by the pronounced blue-to-red areas on the differential image. At present, the inventors have not methodologically been able to perform MWT experiments while simultaneously monitoring of the compartmental pressure as an independent marker of an injury. However, a visual inspection revealed clear evidence of swelling. Additionally, after immediate infusion of a lactate ringer solution into the muscular compartment, a decrease in arterial blood flow (down 20%) was observed, indicating an elevation in the compartmental pressure.

The percentage change in the experiments is significant. For example, in the case of a simulated compartment syndrome presented in FIGS. 15A-15B and FIGS. 16A-16B, the maximal changes at +5 min in the development of injury (FIGS. 15A and 15B) are about 20% for both $\in$' and $\in$" (blue color), while at +16 min in the development of injury (FIGS. 16A and 16B) the maximal changes are much larger, about +38% for $\in$' and about +100% for $\in$" (red color). It will be appreciated that in this case the frequency was 1.05 GHz; overall, the changes are more localized and more pronounced, especially on $\in$", at higher frequencies, as demonstrated by comparing FIGS. 17A-17B and FIGS. 18A-18B, where the operational frequency was 1.5 GHz, to FIGS. 15A-15B and FIGS. 16A-16B.

Examples: 2D Computer Head Model

The initial applicability of the novel electromagnetic imaging concept for brain imaging was assessed using 2D computer model of a head.

Figure 19A:
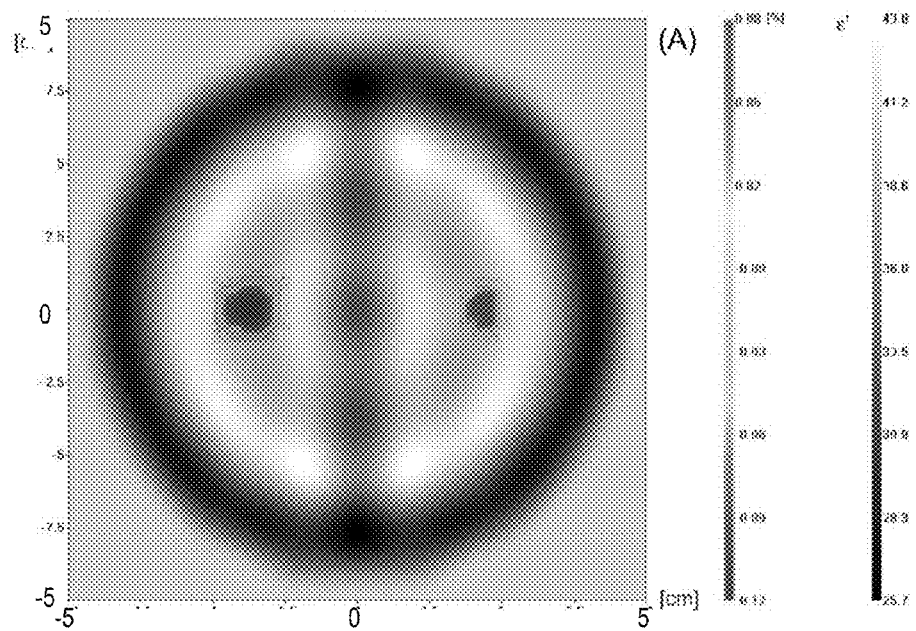
FIGS. 19A and 19B are imaging results presented as fused images, in simplified 2D geometry, of a stroke injury, wherein the operational frequency was 1.0 GHz.
Figure 19B:
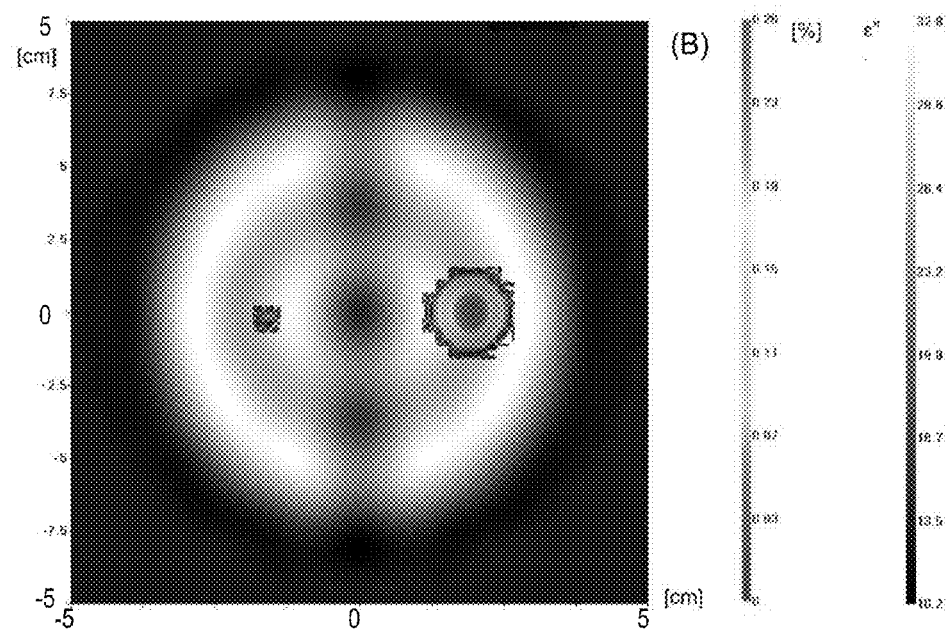

FIGS. 19A and 19B are imaging results presented as fused images, in simplified 2D geometry, of a stroke injury, wherein the operational frequency was 1.0 GHz. In this experiment, two small (radius of 1 mm) inhomogeneities with −10% and +10% dielectric contrasts were added to the model to simulate small stroke areas of different nature. The top imaging result (FIG. 19A) presents a fused image of $\in$' and the bottom imaging result (FIG. 19B) presents a fused image of $\in$". The background images in the gray palette are the absolute images of the head model. Absolute images were reconstructed using non-linear Newton inversion of scattered electromagnetic fields from 64 receivers, equidistantly positioned in a circle (radius=11 cm) around a head. On the top of the background images are differential images presented in color. The differential images were obtained as differences between two reconstructed absolute images: an image of a normal head and an image of a head with two small areas of different circulation, simulating two types of stroke. As can be appreciated from FIGS. 19A and 19B, two small (radius of 1 mm) stroke areas are clearly identified. These results demonstrate an applicability of the technology for not only a fast assessment of stroke injury, but also suggest tremendous potentials for functional neuroimaging as an alternative to functional MRI with a clear advance in terms of time resolution.

Figure 20:
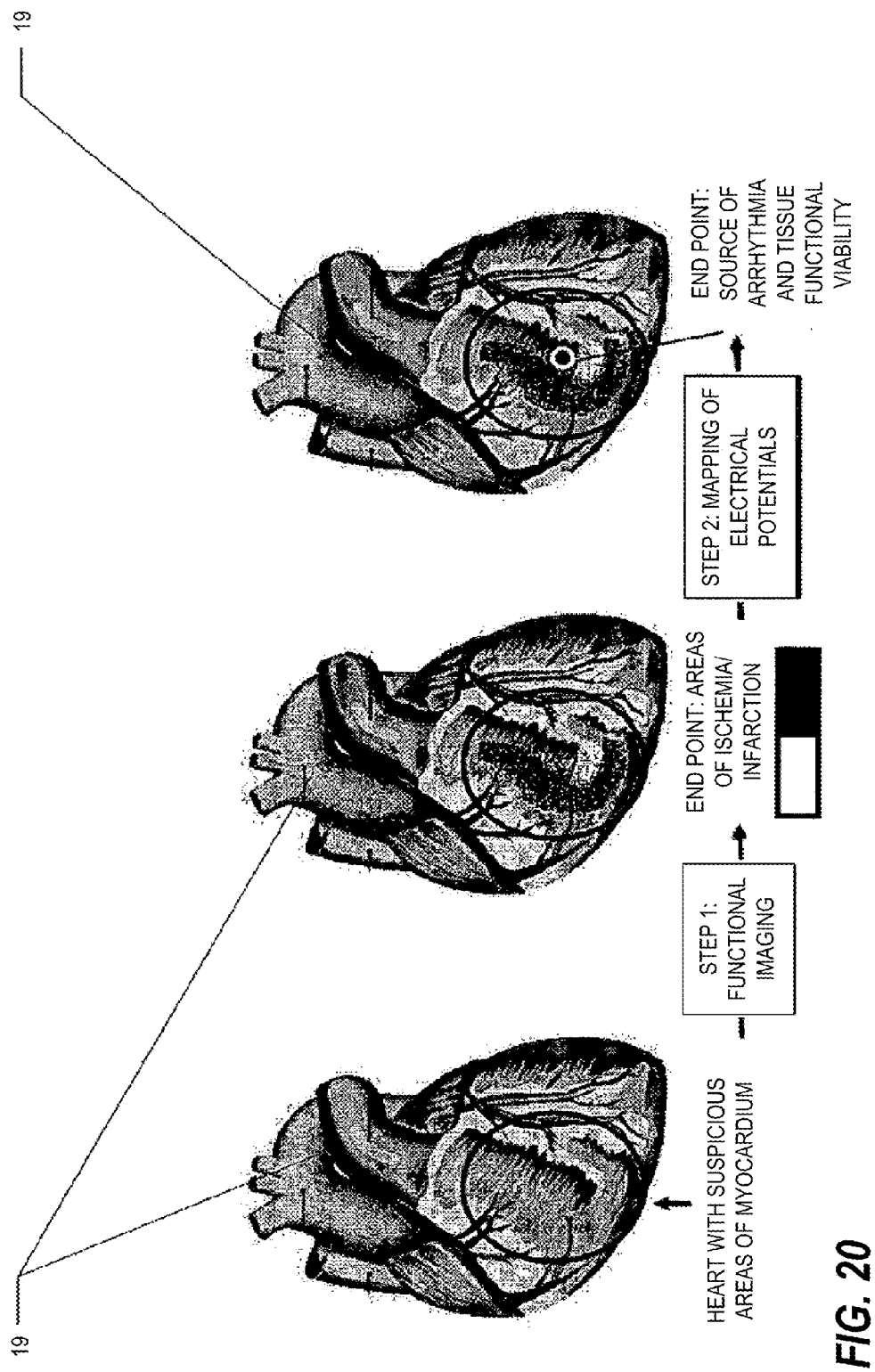
FIG. 20 is an illustration of an exemplary application of functional imaging and non-invasive electrical potential mapping according to a method of the present invention.

FIG. 20 is an illustration of an exemplary application of functional imaging and non-invasive electrical potential mapping according to a method of the present invention. As will be appreciated, the system and methodology of the present invention allow for both functional imaging of biological objects 19 and mapping of electrical excitation within biological tissues 19. This may be achieved as a two-step imaging process, as illustrated in FIG. 20. First, the system 100 is used as an electromagnetic tomographic imaging tool for non-invasive assessment of functional and pathological conditions of a biological object 19 and the location of any areas of diseased tissues 19. For example, in FIG. 20, cardiac tissue with suspicious areas of myocardium is functionally imaged in Step 1 to identify areas of ischemia/infarction. Second, if the location of a diseased target is within a biologically excited tissue 19 (such as cardiac tissue, nervous tissue, musculoskeletal tissue, or the like), then a dielectric contrast (sensitive) substance/solution (for example, a suspension of nanoparticles) may be injected into the tissue (circulation system), thus allowing for non-invasive mapping of electrical excitation and the location of a source of irregularity (arrhythmogenety). Since the functional/pathological condition of the tissue in and near this source is known from the first step of the EM field imaging, it allows for unique and extremely valuable information to be developed for use in determining tissue viability and in choosing a strategy of further treatment and therapy. For example, in FIG. 20, electrical potentials in the areas of ischemia/infarction in the cardiac tissue are mapped to identify possible sources of arrhythmia and tissue functional viability. Further, if an ablation of this tissue is chosen than the same system can be used and electromagnetic energy can be focused precisely into the target area according to known techniques such as those described in U.S. Pat. Nos. 5,715,819, 6,026,173 and 6,333,087, each of which is incorporated herein by reference.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A method for functional imaging of, and non-invasive assessment of a spread of electrical excitation within, biological tissues, the method comprising:

first, carrying out an electromagnetic tomographic imaging process to generate a baseline anatomical image of a biological tissue;

thereafter, repeatedly:
carrying out the electromagnetic tomographic imaging process to generate successive images of the biological tissue,
comparing each successive image to a previous image to determine a distribution of relative physiological change across the biological tissue, wherein the relative physiological change is expressed as a percentage change, and
from the comparison, generating a differential image that illustrates the distribution of relative physiological change across the biological tissue; and combining at least one of the successive differential images indicating relative physiological change with the baseline anatomical image for display as a single unified image in which both the anatomy of the biological tissue and the distribution of relative physiological change across the biological tissue are included and are separately recognizable from one another;

wherein the electromagnetic tomographic imaging process includes:
providing a plurality of electromagnetic field sources for generating an electromagnetic field domain in a target area,
providing a plurality of electromagnetic field detectors for detecting at least a portion of the electromagnetic field domain in the target area,
positioning a biological tissue within the target area,
generating an electromagnetic field domain via a selected plurality of the electromagnetic field sources,
selectively characterizing the electromagnetic field generated by each electromagnetic field source so that each of a selected plurality of electromagnetic field detectors recognizes a source of electromagnetic field from a plurality of electromagnetic field sources,
controlling the electromagnetic field sources and the electromagnetic field detectors, so that electromagnetic fields generated by the selected plurality of electromagnetic field sources are received by the selected plurality of the electromagnetic field detectors after interacting with the biological tissue,
based at least in part upon the electromagnetic field received at each electromagnetic field detector, measuring interference characteristics of at least an electromagnetic field generated by the biological tissue, and
determining image information, pertaining to the biological tissue, from the measured interference characteristics.

2. The method of claim 1, further comprising a preliminary step of entering, into an imaging computer that controls operation of the method, a time duration of executing the repeated steps of carrying out the electromagnetic tomographic imaging process to generate successive images of the biological tissue, comparing each successive image to a previous image to determine a relative physiological change in the biological tissue, and from the comparison, generating a differential image that illustrates the amount of relative physiological change.

3. The method of claim 2, wherein the time duration is entered as a unit of time.

4. The method of claim 2, wherein the time duration is entered as a number of cycles of physiological activity.

5. The method of claim 1, further comprising a preliminary step of entering, into an imaging computer that controls operation of the method, a type of imaging study to be conducted.

6. The method of claim 5, wherein the biological tissue is a soft tissue of extremity or myocardial tissue or brain tissue, and wherein the method is carried out as part of a dynamic study of normal physiological activity within the biological tissue.

7. The method of claim 5, wherein the biological tissue is myocardium or muscle tissue, and wherein the method is carried out as part of a controlled stress study to assess a functional viability of the biological tissue during exercise or other physical stress.

8. The method of claim 5, wherein the biological tissue is myocardium or muscle tissue, and wherein the method is carried out as part of a controlled stress study to assess a functional viability of the biological tissue during pharmacologically induced stress.

9. The method of claim 1, further comprising a step of calculating system parameters, via an imaging computer that controls operation of the method, based on a time duration entered by a user, a type of imaging study entered by a user, or both.

10. The method of claim 9, wherein the parameters include one or more of a required timely resolution, a number of frames to be acquired by the imaging computer, a required accuracy of measurements in amplitude, a required accuracy of measurements in phase, and a required accuracy of measurements in polarization.

11. The method of claim 1, further comprising a step of injecting an electromagnetic contrast agent into the biological tissue.

12. The method of claim 1, wherein the repeated step of carrying out the electromagnetic tomographic imaging process to generate successive images of the biological tissue utilizes the most recent image as a starting point in generating the next successive image.

13. The method of claim 1, wherein the electromagnetic tomographic imaging process further comprises a step of applying a motion correction operation to minimize the effects of motion of the body tissue during the process.

14. The method of claim 1, wherein baseline anatomical imagery is represented via darker and lighter shades of gray, and relative physiological change is represented via various colors superimposed over the gray anatomical imagery.

15. The method of claim 1, wherein various different colors are used to represent different values of percentage change.

16. A method for functional imaging of, and non-invasive assessment of a spread of electrical excitation within, biological tissues, the method comprising:
first, carrying out an electromagnetic tomographic imaging process to generate a baseline anatomical image of a biological tissue;
thereafter, carrying out the electromagnetic tomographic imaging process to generate a later image of the biological tissue;
comparing the later image to a previous image to determine a relative amount of physiological change in areas across the biological tissue, wherein the relative amount of physiological change is expressed as a percentage change;
generating image information reflecting the relative amount of physiological change, as determined in the comparing step, in the areas across the biological tissue;
combining the generated image information with the baseline anatomical image; and
displaying the result of the combining step as a single unified image so as to present the relative amount of physiological change, expressed as a percentage change, against a backdrop of the baseline anatomical image;
wherein the electromagnetic tomographic imaging process includes:
providing a plurality of electromagnetic field sources for generating an electromagnetic field domain in a target area,
providing a plurality of electromagnetic field detectors for detecting at least a portion of the electromagnetic field domain in the target area,
positioning a biological tissue within the target area,
generating an electromagnetic field domain via a selected plurality of the electromagnetic field sources,
selectively characterizing the electromagnetic field generated by each electromagnetic field source so that each of a selected plurality of electromagnetic field detectors recognizes a source of electromagnetic field from a plurality of electromagnetic field sources,
controlling the electromagnetic field sources and the electromagnetic field detectors, so that electromagnetic fields generated by the selected plurality of electromagnetic field sources are received by the selected plurality of the electromagnetic field detectors after interacting with the biological tissue,
based at least in part upon the electromagnetic field received at each electromagnetic field detector, measuring interference characteristics of at least an electromagnetic field generated by the biological tissue, and
determining image information, pertaining to the biological tissue, from the measured interference characteristics.

17. A method for functional imaging of, and non-invasive assessment of a spread of electrical excitation within, biological tissues, the method comprising:
(a) first, carrying out an electromagnetic tomographic imaging process to generate a baseline anatomical image of a biological tissue, wherein the image is created by plotting, at each relevant point in the image area, the dielectric permittivity of the biological tissue at that point at the baseline time;
(b) thereafter, repeatedly:
(i) carrying out the electromagnetic tomographic imaging process to generate successive anatomical images of the biological tissue, wherein each image is created by plotting, at each relevant point in the image area, the dielectric permittivity of the biological tissue at that point at the time of the respective iteration of the imaging process,
(ii) comparing the dielectric permittivity at each point at each respective time with the dielectric permittivity at the respective point at the baseline time,
(iii) from the comparison, determining the change in dielectric permittivity that has occurred at each point at the time of the respective iteration of the imaging process, relative to the dielectric permittivity at the respective point at the baseline time, (iv) for each point, calculating a percentage change in dielectric permittivity that has occurred at the time of the respective iteration of the imaging process, relative to the dielectric permittivity at the respective point at the baseline time, and (v) generating an image of relative physiological change in the biological tissue, relative to biological tissue at the baseline time, wherein the image is created by plotting, at each relevant point in the image area, the calculated percentage change;

(c) wherein the electromagnetic tomographic imaging process includes:

(i) providing a plurality of electromagnetic field sources for generating an electromagnetic field domain in a target area, (ii) providing a plurality of electromagnetic field detectors for detecting at least a portion of the electromagnetic field domain in the target area, (iii) positioning a biological tissue within the target area, (iv) generating an electromagnetic field domain via a selected plurality of the electromagnetic field sources, (v) selectively characterizing the electromagnetic field generated by each electromagnetic field source so that each of a selected plurality of electromagnetic field detectors recognizes a source of electromagnetic field from a plurality of electromagnetic field sources, (vi) controlling the electromagnetic field sources and the electromagnetic field detectors, so that electromagnetic fields generated by the selected plurality of electromagnetic field sources are received by the selected plurality of the electromagnetic field detectors after interacting with the biological tissue, (vii) based at least in part upon the electromagnetic field received at each electromagnetic field detector, measuring interference characteristics of at least an electromagnetic field generated by the biological tissue, and (viii) determining image information, pertaining to the biological tissue, from the measured interference characteristics, the image information being in the form of dielectric permittivities for various points in the biological tissue.

18. The method of claim 17, wherein the successive images from the repeated iterations of the image generation process demonstrate the gradual spread of an electrical excitation.

19. The method of claim 17, further comprising a step of generating a further image that is a combination of the baseline anatomical image and the image of relative physiological change, wherein, in the image area, a first type of visual indicia represents the anatomy of the biological tissue and a second type of visual indicia represents the relative physiological change, the first and second types of visual indicia being overlaid on top of each other such that anatomy information and calculated percentage change information are simultaneously visible, wherein the relative physiological change is expressed as a percentage change.

* * * * *